(12) United States Patent
Martinez et al.

(10) Patent No.: US 10,512,623 B2
(45) Date of Patent: Dec. 24, 2019

(54) PHARMACEUTICALLY ACCEPTABLE SALTS OF B-GUANIDINOPROPIONIC ACID WITH IMPROVED PROPERTIES AND USES THEREOF

(71) Applicant: Rgenix, Inc., New York, NY (US)

(72) Inventors: Eduardo J. Martinez, Bryn Mawr, PA (US); Andreas G. Grill, Saint James, NY (US); Aniruddh Singh, Carteret, NJ (US); Padmini Kavuru, Fitchburg, MA (US)

(73) Assignee: Rgenix, Inc., New York, NY (US)

( * ) Notice: Subject to any disclaimer, the term of this patent is extended or adjusted under 35 U.S.C. 154(b) by 0 days.

(21) Appl. No.: 15/795,540

(22) Filed: Oct. 27, 2017

(65) Prior Publication Data
US 2018/0243248 A1 Aug. 30, 2018

Related U.S. Application Data

(63) Continuation of application No. 15/281,329, filed on Sep. 30, 2016, now Pat. No. 9,827,217, which is a continuation of application No. 15/245,750, filed on Aug. 24, 2016, now abandoned.

(60) Provisional application No. 62/209,624, filed on Aug. 25, 2015.

(51) Int. Cl.
*A61K 31/197* (2006.01)
*A61K 47/14* (2017.01)
*A61K 47/12* (2006.01)
*C07C 279/14* (2006.01)
*C07C 57/15* (2006.01)
*A61K 9/00* (2006.01)

(52) U.S. Cl.
CPC ........... *A61K 31/197* (2013.01); *A61K 47/12* (2013.01); *C07C 57/15* (2013.01); *C07C 279/14* (2013.01); *A61K 9/0019* (2013.01)

(58) Field of Classification Search
CPC .............................. A61K 31/197; A61K 47/14
See application file for complete search history.

(56) References Cited

U.S. PATENT DOCUMENTS

| | | |
|---|---|---|
| 3,870,709 A | 3/1975 | Hamanaka |
| 3,933,797 A | 1/1976 | Hamanaka |
| 3,972,872 A | 8/1976 | Hamanaka |
| 5,750,193 A | 5/1998 | Nass et al. |
| 5,955,617 A | 9/1999 | Larsen et al. |
| 5,994,577 A | 11/1999 | Larsen et al. |
| 6,166,080 A | 12/2000 | Larsen et al. |
| 6,177,453 B1 | 1/2001 | Larsen et al. |
| 6,184,216 B1 | 2/2001 | Larsen et al. |
| 6,242,491 B1 | 6/2001 | Kaddurah-Daouk |
| 6,274,580 B1 | 8/2001 | Larsen et al. |
| 6,329,403 B1 | 12/2001 | Odaka et al. |
| 6,329,545 B1 | 12/2001 | Larsen et al. |
| 6,348,200 B1 | 2/2002 | Nakajima et al. |
| 6,605,115 B1 | 8/2003 | Cooke et al. |
| 7,186,754 B2 | 3/2007 | Kaddurah-Daouk |
| 7,273,846 B2 | 9/2007 | Bednarek |
| 8,101,661 B2 | 1/2012 | Mickle |
| 8,118,884 B2 | 2/2012 | Ascione et al. |
| 8,685,916 B2 | 4/2014 | Jenkins et al. |
| 8,748,567 B2 | 6/2014 | Narasimhaswamy et al. |
| 8,765,115 B2 | 7/2014 | Fujiwara et al. |
| 8,927,500 B2 | 1/2015 | Guerlavais et al. |
| 8,937,090 B2 | 1/2015 | Kaminuma et al. |
| 9,040,497 B2 | 5/2015 | Tavazoie et al. |
| 9,492,414 B2 | 11/2016 | Tavazoie et al. |
| 9,827,217 B2 | 11/2017 | Martinez et al. |
| 9,884,813 B1 | 2/2018 | Martinez et al. |
| 2002/0049253 A1 | 4/2002 | Kaddurah-Daouk |
| 2002/0082448 A1 | 6/2002 | Larsen et al. |
| 2002/0086885 A1 | 7/2002 | Odaka et al. |
| 2004/0074504 A1 | 4/2004 | Cooke et al. |
| 2004/0126366 A1 | 7/2004 | Kaddurah-Daouk et al. |
| 2005/0020492 A1 | 1/2005 | Bednarek |
| 2005/0186158 A1 | 8/2005 | Kaddurah-Daouk |
| 2005/0186194 A1 | 8/2005 | Kaddurah-Daouk |
| 2005/0186195 A1 | 8/2005 | Kaddurah-Daouk |
| 2005/0226840 A1 | 10/2005 | Kaddurah-Daouk |

(Continued)

FOREIGN PATENT DOCUMENTS

| | | |
|---|---|---|
| CA | 101653 A | 8/1977 |
| CA | 2202265 A1 | 5/1996 |

(Continued)

OTHER PUBLICATIONS

Ohira et al. Biochimica & Biophysica Acta, 1995, vol. 1243, Iss. 3, pp. 367-372.*

(Continued)

*Primary Examiner* — Samira J Jean-Louis
(74) *Attorney, Agent, or Firm* — Clark & Elbing LLP

(57) ABSTRACT

The present invention relates to new pharmaceutical salts of β-GPA which exhibit improved physical properties. In particular, the invention relates to salts of β-GPA with improved flow properties (e.g., improved Carr's index and/or Hausner ratio) such as fumarate salts, succinate salts, and oxalate salts. The invention also relates to pharmaceutical compositions including a pharmaceutically effective amount of one or more salts of β-GPA, as well as methods of treating cancer including administration of a formulation including a β-GPA salt of the invention to a subject in need thereof.

15 Claims, 37 Drawing Sheets

(56) References Cited

U.S. PATENT DOCUMENTS

| | | |
|---|---|---|
| 2005/0227996 A1 | 10/2005 | Kaddurah-Daouk |
| 2006/0159719 A1 | 7/2006 | Cooke et al. |
| 2006/0167402 A1 | 7/2006 | Cooke et al. |
| 2006/0241021 A1 | 10/2006 | Kaddurah-Daouk et al. |
| 2007/0027090 A1 | 2/2007 | Kaddurah-Daouk et al. |
| 2007/0253944 A1 | 11/2007 | Kaddurah-Daouk |
| 2009/0221706 A1 | 9/2009 | Kaddurah-Daouk et al. |
| 2010/0113353 A1 | 5/2010 | Cooke et al. |
| 2010/0179106 A1 | 7/2010 | Khan |
| 2010/0226870 A1 | 9/2010 | Kaddurah-Daouk |
| 2010/0233084 A1 | 9/2010 | Narasimhaswamy et al. |
| 2010/0292336 A1 | 11/2010 | Mickle |
| 2010/0292337 A1 | 11/2010 | Mickle |
| 2010/0329997 A1 | 12/2010 | Kaddurah-Daouk |
| 2011/0008272 A1 | 1/2011 | Kaddurah-Daouk |
| 2011/0021632 A1 | 1/2011 | Kaddurah-Daouk |
| 2011/0085993 A1 | 4/2011 | Kaddurah-Daouk |
| 2011/0158925 A1 | 6/2011 | Ascione et al. |
| 2011/0262355 A1 | 10/2011 | Jenkins et al. |
| 2011/0262359 A1 | 10/2011 | Jenkins et al. |
| 2012/0141391 A1 | 6/2012 | Kaddurah-Daouk |
| 2012/0232066 A1 | 9/2012 | Jenkins et al. |
| 2012/0232111 A1 | 9/2012 | Kaminuma et al. |
| 2012/0245211 A1 | 9/2012 | Clark et al. |
| 2012/0295834 A1 | 11/2012 | Jenkins et al. |
| 2012/0328561 A1 | 12/2012 | Fujiwara et al. |
| 2013/0011364 A1 | 1/2013 | Fichert et al. |
| 2013/0021085 A1 | 1/2013 | Kumar et al. |
| 2013/0040877 A1 | 2/2013 | Kofoed et al. |
| 2013/0058958 A1 | 3/2013 | Bowen et al. |
| 2013/0059914 A1 | 3/2013 | Jenkins et al. |
| 2013/0072462 A1 | 3/2013 | Khan |
| 2013/0090488 A1 | 4/2013 | Dietz |
| 2013/0123169 A1 | 5/2013 | Kawahata et al. |
| 2013/0210701 A1 | 8/2013 | Jenkins et al. |
| 2013/0210745 A1 | 8/2013 | Guerlavais et al. |
| 2013/0274205 A1 | 10/2013 | Guerlavais et al. |
| 2013/0281324 A1 | 10/2013 | Gouliaev et al. |
| 2013/0281410 A1 | 10/2013 | Renshaw |
| 2014/0045798 A1 | 2/2014 | Khan |
| 2014/0121152 A1 | 5/2014 | Jenkins et al. |
| 2014/0141069 A1 | 5/2014 | Brewster |
| 2014/0206597 A1 | 7/2014 | Jenkins et al. |
| 2014/0224737 A1 | 8/2014 | Fichert et al. |
| 2014/0294727 A1 | 10/2014 | Narashimhasway et al. |
| 2014/0378534 A1* | 12/2014 | Tavazoie ............ A61K 31/7072 514/44 A |
| 2015/0051155 A1 | 2/2015 | Guerlavais et al. |
| 2015/0126520 A1 | 5/2015 | Chiodo et al. |
| 2017/0056352 A1 | 3/2017 | Martinez et al. |
| 2017/0056353 A1 | 3/2017 | Martinez et al. |

FOREIGN PATENT DOCUMENTS

| | | |
|---|---|---|
| CA | 2329004 A1 | 1/2000 |
| CA | 2376375 A1 | 12/2000 |
| CA | 2376943 A1 | 1/2001 |
| CA | 2473229 A1 | 7/2003 |
| CA | 2698755 A1 | 3/2009 |
| CA | 2795222 A1 | 10/2011 |
| CA | 2801624 A1 | 12/2011 |
| CA | 2827662 A1 | 9/2012 |
| CA | 2852468 A1 | 4/2013 |
| CA | 2862038 A1 | 8/2013 |
| CA | 2864120 A1 | 8/2013 |
| CN | 102850242 A | 1/2013 |
| CN | 103288685 A | 9/2013 |
| EP | 0260118 A1 | 3/1988 |
| EP | 0426100 A1 | 5/1991 |
| EP | 1656945 A1 | 5/2006 |
| EP | 1746099 A1 | 1/2007 |
| EP | 1880711 A1 | 1/2008 |
| EP | 2397127 A1 | 12/2011 |
| EP | 2399885 A1 | 12/2011 |
| EP | 2567705 A2 | 3/2013 |
| GB | 1379502 A | 1/1975 |
| JP | 3745439 B2 | 2/2006 |
| JP | 4317599 B2 | 8/2009 |
| JP | 2010-143922 A | 7/2010 |
| JP | 2010-143928 A | 7/2010 |
| JP | 2010-260861 A | 11/2010 |
| WO | WO-96/16031 A1 | 5/1996 |
| WO | WO-97/14401 A1 | 4/1997 |
| WO | WO-97/44324 A1 | 11/1997 |
| WO | WO-00/00195 A1 | 1/2000 |
| WO | WO-00/74701 A2 | 12/2000 |
| WO | WO-01/00203 A1 | 1/2001 |
| WO | WO-03/013574 A1 | 2/2003 |
| WO | WO-03/039449 A2 | 5/2003 |
| WO | WO-03/060091 A2 | 7/2003 |
| WO | WO-03/101402 A2 | 12/2003 |
| WO | WO-2004/069232 A2 | 8/2004 |
| WO | WO-2007/014756 A1 | 2/2007 |
| WO | WO-2008/043024 A2 | 4/2008 |
| WO | WO-2008/054544 A2 | 5/2008 |
| WO | WO-2008/092591 A2 | 8/2008 |
| WO | WO-2009/033130 A1 | 3/2009 |
| WO | WO-2009/098142 A1 | 8/2009 |
| WO | WO-2010/070243 A1 | 6/2010 |
| WO | WO-2011/082076 A1 | 7/2011 |
| WO | WO-2011/121008 A1 | 10/2011 |
| WO | WO-2011/127933 A1 | 10/2011 |
| WO | WO-2011/133149 A1 | 10/2011 |
| WO | WO-2011/133150 A1 | 10/2011 |
| WO | WO-2011/133348 A1 | 10/2011 |
| WO | WO-2011/139718 A1 | 11/2011 |
| WO | WO-2011/143534 A1 | 11/2011 |
| WO | WO-2011/160857 A2 | 12/2011 |
| WO | WO-2012/024611 A1 | 2/2012 |
| WO | WO-2012/047630 A2 | 4/2012 |
| WO | WO-2012/122412 A2 | 9/2012 |
| WO | WO-2012/122420 A2 | 9/2012 |
| WO | WO-2012/122422 A2 | 9/2012 |
| WO | WO-2012/138214 A1 | 10/2012 |
| WO | WO-2012/173846 A2 | 12/2012 |
| WO | WO-2013/016668 A2 | 1/2013 |
| WO | WO-2013/059525 A1 | 4/2013 |
| WO | WO-2013/083642 A1 | 6/2013 |
| WO | WO-2013/123266 A1 | 8/2013 |
| WO | WO-2013/123267 A1 | 8/2013 |
| WO | WO-2013/183055 A1 | 12/2013 |
| WO | WO-2014/071067 A2 | 5/2014 |
| WO | WO-2014/072490 A1 | 5/2014 |
| WO | WO-2014/138492 A1 | 9/2014 |
| WO | WO-2017/035331 A1 | 3/2017 |

OTHER PUBLICATIONS

Loo et al. Cell, 2015, vol. 160, pp. 393-406.*
International Search Report and Written Opinion for International Patent Application No. PCT/US2016/048643, dated Oct. 25, 2016 (14 pages).
International Preliminary Report on Patentability for International Application No. PCT/US2016/048643, dated Feb. 27, 2018 (6 pages).
Dietrich et al., "Carbon-13 Nuclear Magnetic Resonance Studies of Creatine, Creatinine and some of their Analogs," Org Magnet Res. 13(2):79-88 (1980).
Extended European Search Report for European Application No. 16840104.0, dated Mar. 1, 2019 (8 pages).
Holm et al., "Mitteilungen aus dem pharmazeutisch-chemischen Institut der Universität Marburg," Archiv De Pharmazie. 242:590-612 (1904).
Rodionow et al., Zhurnal Obshchei Khimi; 18:2023-2032 (1948).

* cited by examiner

FIGS. 29A-J

PHARMACEUTICALLY ACCEPTABLE SALTS OF β-GUANIDINOPROPIONIC ACID WITH IMPROVED PROPERTIES AND USES THEREOF

BACKGROUND

β-Guanidinopropionic acid (β-GPA), also referred to as guanidinopropionic acid, beta-guanidinopropionic acid or, N-(aminoiminomethyl)-beta-alanine is a creatine analog. Studies on animals (rats, monkeys, hamsters) show that acidic guanidine derivatives such as β-GPA can ameliorate hyperglycemia in animal models of noninsulin-dependent diabetes. Accordingly, it is sometimes used as a dietary supplement in diabetic patients to regulate blood sugar levels. β-GPA is a white crystalline powder that is highly soluble in water (>50 mg/mL).

β-GPA has recently been found to be effective for the suppression of metastasis, particularly liver metastasis in gastrointestinal cancers, e.g., see International Patent Publication WO2014/071067. However, due to the physical properties of β-GPA in the solid state, e.g., poor flow properties and compressibility, there exists a need for β-GPA salts and formulations with improved physical properties and handling characteristics.

SUMMARY OF THE INVENTION

The present invention features new pharmaceutical salts of β-GPA which exhibit improved physical properties. In particular, the invention features salts of β-GPA with improved flow properties (e.g., improved Carr's index and/or Hausner ratio), such as fumarate salts, succinate salts, and oxalate salts. The invention also features pharmaceutical compositions including a pharmaceutically effective amount of one or more salts of β-GPA, as well as methods of treating cancer including administration of a formulation including a β-GPA salt of the invention to a subject in need thereof.

Accordingly, in a first aspect, the invention features a pharmaceutically acceptable salt of β-guanidinopropionic acid having a Carr's Index of less than 20 (e.g., less than 15, less than 10, less than 6) and/or a Hausner ratio of less than 1.25 (e.g., less than 1.2, less than 1.15, less than 1.1). In some embodiments, the pharmaceutically acceptable salt is a salt of a dicarboxylic acid (e.g., fumaric acid, succinic acid, or oxalic acid). In some embodiments, the pharmaceutically acceptable salt is a fumarate salt (e.g., a 1:1 fumarate salt), a succinate salt (e.g., a 2:1 succinate salt), or an oxalate salt (e.g., a 1:1 oxalate salt).

In some embodiments, the pharmaceutically acceptable salt is crystalline (e.g., a 1:1 fumarate salt with rod-like crystal morphology. In some embodiments, the pharmaceutically acceptable salt includes less than 40% by weight (e.g., less than 30%, less than 20%, less than 10%, less than 5%, less than 1% or between 30-40%, 25-35%, 20-30%, 15-25%, 10-20%, 5-15%, 1-10%) of amorphous compound. In some embodiments, the pharmaceutically acceptable salt is substantially free of amorphous compound. In some embodiments, the pharmaceutically acceptable salt is substantially free of any other salt or crystal form of β-GPA.

In some embodiments, the pharmaceutically acceptable salt is a 1:1 fumarate salt. In some embodiments, the pharmaceutically acceptable salt has an endothermic onset at about 171° C. (e.g., from 169° C. to 173° C., 170° C. to 173° C., 169° C. to 172° C., 170° C. to 172° C.) in differential scanning calorimetry (DSC) profile. In some embodiments, the pharmaceutically acceptable salt has a loss of weight from 31° C. to 140° C. of less than 5% (e.g., less than 4%, less than 3%, less than 2%, less than 1%) as measured by thermal gravimetric analysis.

In some embodiments, the pharmaceutically acceptable salt has at least one peak at diffraction angle 2θ (°) of 20±0.5 as measured by X-ray powder diffractometry. In some embodiments, the pharmaceutically acceptable salt further has at least one peak at diffraction angle 2θ (°) of 20±0.5, 20.5±0.5, and/or 23±0.5 as measured by X-ray powder diffractometry. In some embodiments, the pharmaceutically acceptable salt has one or more (e.g., two or more, three or more, four or more, five or more, six or more, seven or more, eight or more, nine or more, ten or more, eleven or more, twelve or more, thirteen or more, fourteen or more) peaks listed in Table 1 as measured by X-ray powder diffractometry. In some embodiments, the pharmaceutically acceptable salt has all of the peaks listed in Table 1 as measured by X-ray powder diffractometry.

TABLE 1

| XRPD peak list for the 1:1 fumarate salt of β-GPA | |
|---|---|
| 2θ (°) | Intensity |
| 11.78 | 5.5 |
| 13.95 | 6.0 |
| 17.42 | 6.4 |
| 19.22 | 12.5 |
| 19.68 | 21.1 |
| 20.02 | 8.4 |
| 20.58 | 27.4 |
| 21.01 | 6.3 |
| 22.87 | 22.4 |
| 23.74 | 6.4 |
| 24.74 | 5.5 |
| 25.57 | 5.4 |
| 26.74 | 100 |
| 28.84 | 12.3 |
| 29.48 | 7.1 |

In some embodiments, the pharmaceutically acceptable salt has at least one peak at 3300±1 cm$^{-1}$ as measured by Raman spectroscopy. In some embodiments, the pharmaceutically acceptable salt has at least one peak at 3188±1 cm$^{-1}$ as measured by Raman spectroscopy. In some embodiments, the pharmaceutically acceptable salt has at least one peak at 3049±1 cm$^{-1}$ as measured by Raman spectroscopy. In some embodiments, the pharmaceutically acceptable salt has at least one peak at 2941±1 cm$^{-1}$ as measured by Raman spectroscopy. In some embodiments, the pharmaceutically acceptable salt has at least one peak at 2886±1 cm$^{-1}$ as measured by Raman spectroscopy. In some embodiments, the pharmaceutically acceptable salt has at least one peak at 1713±1 cm$^{-1}$ as measured by Raman spectroscopy. In some embodiments, the pharmaceutically acceptable salt has at least one peak at 1653±1 cm$^{-1}$ as measured by Raman spectroscopy. In some embodiments, the pharmaceutically acceptable salt has at least one peak at 1483±1 cm$^{-1}$ as measured by Raman spectroscopy. In some embodiments, the pharmaceutically acceptable salt has at least one peak at 1421±1 cm$^{-1}$ as measured by Raman spectroscopy. In some embodiments, the pharmaceutically acceptable salt has at least one peak at 1382±1 cm$^{-1}$ as measured by Raman spectroscopy. In some embodiments, the pharmaceutically acceptable salt has at least one peak at 1305±1 cm$^{-1}$ as measured by Raman spectroscopy. In some embodiments, the pharmaceutically acceptable salt has at least one peak at 1268±1 cm$^{-1}$ as measured by Raman spectroscopy. In some embodiments, the pharmaceutically acceptable salt has at least one peak at 1190±1 cm$^{-1}$ as measured by Raman spectroscopy. In some embodiments, the pharmaceutically acceptable salt has at least one peak at 1084±1 cm$^{-1}$ as measured by Raman spectroscopy. In some embodiments, the pharmaceutically acceptable salt has at least one peak at 997±1 cm$^{-1}$ as measured by Raman spectroscopy. In some embodiments, the pharmaceutically acceptable salt has at least one peak at 896±1 cm$^{-1}$ as measured by Raman spectroscopy. In some embodiments, the pharmaceutically acceptable salt has at least one peak at 681±1 cm$^{-1}$ as measured by Raman spectroscopy. In some embodiments, the pharmaceutically acceptable salt has at least one peak at 625±1 cm$^{-1}$ as measured by Raman spectroscopy. In some embodiments, the pharmaceutically acceptable salt has at least one peak at 555±1 cm$^{-1}$ as measured by Raman spectroscopy. In some embodiments, the pharmaceutically acceptable salt has at least one peak at 486±1 cm$^{-1}$ as measured by Raman spectroscopy. In some embodiments, the pharmaceutically acceptable salt has one or more (e.g., two or more, three or more, four or more, five or more, six or more, seven or more, eight or more, nine or more, ten or more, eleven or more, twelve or more, thirteen or more, fourteen or more) peaks listed in Table 2 as measured by Raman spectroscopy. In some embodiments, the pharmaceutically acceptable salt has all of the peaks listed in Table 2 as measured by Raman spectroscopy.

TABLE 2

Raman spectra peak list for the 1:1 fumarate salt of β-GPA
Raman Shift (cm−1)

| |
|---|
| 3300.48 |
| 3188.58 |
| 3049.73 |
| 2941.74 |
| 2886.78 |
| 1713.28 |
| 1653.49 |
| 1483.79 |
| 1421.11 |
| 1382.54 |
| 1305.4 |
| 1268.76 |
| 1190.66 |
| 1084.59 |
| 997.81 |
| 896.56 |
| 681.53 |
| 625.6 |
| 555.21 |
| 486.79 |

In some embodiments, the pharmaceutically acceptable salt is a 1:1 oxalate salt. In some embodiments, the pharmaceutically acceptable salt has at least one peak at diffraction angle 2θ (°) of 27.5±0.5 as measured by X-ray powder diffractometry. In some embodiments, the pharmaceutically acceptable salt has one or more (e.g., two or more, three or more, four or more, five or more, six or more, seven or more, eight or more, nine or more, ten or more, eleven or more, twelve or more, thirteen or more, fourteen or more) peaks listed in Table 3. In some embodiments, the pharmaceutically acceptable salt has all of the peaks listed in Table 3 as measured by X-ray powder diffractometry.

TABLE 3

XRPD peak list for the 1:1 oxalate salt of β-GPA

| Angle (2Θ) degree | Intensity % |
|---|---|
| 10.66 | 2.1 |
| 14.36 | 1.7 |
| 15.26 | 1.8 |
| 17.79 | 2.0 |
| 20.24 | 2.8 |
| 20.78 | 1.8 |
| 23.69 | 4.0 |
| 26.60 | 1.8 |
| 27.45 | 100.0 |
| 31.50 | 1.7 |
| 33.62 | 1.9 |
| 34.94 | 1.8 |
| 35.76 | 1.7 |
| 36.69 | 1.6 |
| 37.23 | 1.9 |

In some embodiments, the pharmaceutically acceptable salt is a 2:1 succinate salt. In some embodiments, the pharmaceutically acceptable salt has at least one peak at diffraction angle 2θ (°) of 27±0.5 as measured by X-ray powder diffractometry. In some embodiments, the pharmaceutically acceptable salt has one or more (e.g., two or more, three or more, four or more, five or more, six or more, seven or more, eight or more, nine or more, ten or more, eleven or more, twelve or more, thirteen or more, fourteen or more) peaks listed in Table 4. In some embodiments, the pharmaceutically acceptable salt has all of the peaks listed in Table 4 as measured by X-ray powder diffractometry.

TABLE 4

XRPD peak list for the 2:1 succinate salt of β-GPA

| Angle (2Θ) degree | Intensity % |
|---|---|
| 4.87 | 3.9 |
| 16.29 | 4.4 |
| 19.99 | 29.3 |
| 20.62 | 14.8 |
| 22.73 | 3.9 |
| 23.13 | 4.5 |
| 25.60 | 4.5 |
| 26.23 | 4.5 |
| 26.70 | 100.0 |
| 27.26 | 12.4 |
| 31.32 | 4.4 |
| 34.24 | 4.0 |
| 35.19 | 4.6 |
| 36.41 | 4.3 |
| 38.30 | 5.6 |

In another aspect, the invention features a composition (e.g., an aqueous composition) including any of the foregoing pharmaceutically acceptable salts and a pharmaceutically acceptable excipient. In some embodiments, the pharmaceutically acceptable salt contains less than 10% by weight (e.g., less than 5%, less than 1%) of amorphous compound. In some embodiments, the pharmaceutically acceptable salt is substantially free of amorphous compound.

In another aspect, the invention features a composition (e.g., an aqueous composition) including the fumarate salt of β-guanidinopropionic acid, wherein at least 80% (at least 85%, at least 90%, at least 95%, at least 99%) of the fumarate salt of β-guanidinopropionic acid is a 1:1 salt (e.g., wherein the composition is substantially free of the 2:1 fumarate salt of β-guanidinopropionic acid) and a pharmaceutically acceptable excipient.

In some embodiments of any of the foregoing compositions, the pharmaceutically acceptable excipient includes 1,3-butanediol, mannitol, water, Ringer's solution, or isotonic sodium chloride solution. In some embodiments of any of the foregoing compositions, the composition is formulated for intravenous infusion.

In another aspect, the invention features a method for treating cancer (e.g., gastrointestinal cancer such as colon cancer or gastric cancer, pancreatic cancer, liver cancer, breast cancer, prostate cancer, lung cancer, and melanoma) in a subject in need thereof, including administering to the subject an effective amount of any of the foregoing pharmaceutically acceptable salts or compositions.

In another aspect, the invention features a method for treating metastatic cancer (e.g., metastatic gastrointestinal cancer such as colon cancer or gastric cancer) in a subject in need thereof, including administering to the subject an effective amount of any of the foregoing pharmaceutically acceptable salts or compositions. In some embodiments, the effective amount includes an amount effective to suppress metastatic colonization (e.g., metastatic colonization in the liver) of the cancer (e.g., gastrointestinal cancer such as colorectal cancer or gastric cancer).

In another aspect, the invention features a method for treating cancer (e.g., gastrointestinal cancer such as colon cancer or gastric cancer) in a subject in need thereof, comprising injecting into the subject an effective amount of an aqueous composition comprising any of the foregoing pharmaceutically acceptable salts and a pharmaceutically acceptable excipient. In some embodiments, the cancer is metastatic cancer. In some embodiments, the effective amount is an amount effective to suppress metastatic colonization of the cancer.

In another aspect, the invention features a method of treating metastatic cancer (e.g., gastrointestinal cancer such as colorectal cancer, esophageal cancer, or gastric cancer, pancreatic cancer, liver cancer, breast cancer, prostate cancer, lung cancer, and melanoma) in a subject in need thereof comprising: (a) providing a subject identified to have, or to be at risk of having, metastatic cancer on the basis of the expression level of miR-483-5p and/or miR-551a is below a predetermined reference value or the expression level of CKB and/or SLC6a8 is above a predetermined reference value; and (b) administering to the subject an effective amount of any of the foregoing pharmaceutically acceptable salt or compositions.

In some embodiments any of the foregoing methods further include administering an additional therapy (e.g., an additional therapeutic agent) to the subject. In some embodiments, the additional therapy is a therapeutic agent such as cyclocreatine, a RNAi agent, a nucleic acid, a vector, 5-fluorouracil, Oxaliplatin, Irinotecan, Capecitabine, Gemcitabine, Cetuximab, Taxol, Avastin, folinic acid (leucovorin), Regorafenib, Zaltrap, topoisomerase I inhibitors, NKTR-102, Tivantinib, PX-866, Sorafenib, Linifanib, kinase inhibitors, Telatinib, XL281 (BMS-908662), Robatumumab, or IGF1-R inhibitors.

In another aspect, the invention features a method of producing a pharmaceutically acceptable 1:1 fumarate salt of β-guanidinopropionic acid. This method includes combining β-guanidinopropionic acid and fumaric acid in an amount sufficient to produce a pharmaceutically acceptable 1:1 fumarate salt of β-guanidinopropionic acid. In some embodiments, the method includes dissolving the β-guanidinopropionic acid and the fumaric acid in a solvent and the 1:1 fumarate salt of β-guanidinopropionic acid precipitates from the solvent. In some embodiments, the method further includes recrystallization of the 1:1 fumarate salt of β-guanidinopropionic acid.

BRIEF DESCRIPTION OF THE DRAWINGS

FIG. 29A) 1:1 hydrochloride salt of β-GPA; FIG. 29B) 1:1 phosphate salt of β-GPA; FIG. 29C) 1:1 mesylate salt of β-GPA; FIG. 29D) 1:1 maleate salt of β-GPA; FIG. 29E) 1:1 maleate of β-GPA; FIG. 29F) 2:1 maleate salt of β-GPA; FIG. 29G) 1:1 fumarate salt of β-GPA; FIG. 29H) 1:1 malate salt of β-GPA; FIG. 29I) 2:1 succinate salt of β-GPA; and FIG. 29J) 1:1 oxalate salt of β-GPA.

DETAILED DESCRIPTION OF THE INVENTION

Figure 1:
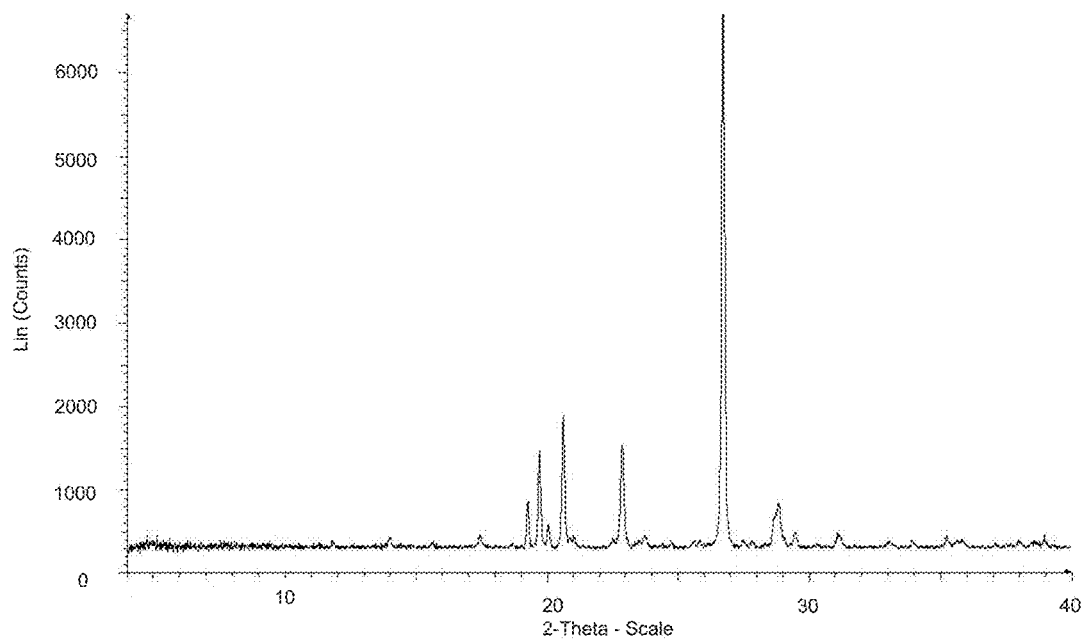
FIG. 1 is an image depicting X-ray powder diffraction (XRPD) pattern obtained for a crystalline form of the 1:1 fumarate salt of β-GPA.

To identify β-GPA salts with improved properties, the present inventors carried out salt screening experiments with 19 different counterions and eight different solvent systems. Ten of the counterions were prepared in crystalline forms and their properties assessed. Following identification of preferred salts with optimal properties, polymorph screening of these salts was conducted.

β-GPA

β-GPA has the structure:

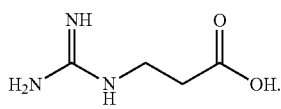

β-GPA is zwitterionic and highly soluble in water (>50 mg/mL), but has low solubility in organic solvents. β-GPA possesses a basic guanidino group, and is thus capable of forming both 1:1 (β-GPA:acid) and 2:1 (β-GPA:acid) salts with diacids. As used herein, a "2:1 salt" of β-GPA with a diacid, e.g., a 2:1 succinate salt, refers to a salt including two molecules of β-GPA and one molecule of the diacid, e.g., a "2:1 succinate salt" includes two molecules of β-GPA and one molecule of succinic acid.

Free β-GPA in solid state is highly crystalline and is generally present as an anhydrate. The crystalline form is non-hygroscopic (e.g., with ~0.3% water uptake at 80% humidity at 25° C.) with a sharp melting point at 219° C. and an endothermic event at 235° C. by DSC. The crystals of β-GPA have a plate-like crystal morphology. No degradation was observed in experiments at 40° C. at 75% humidity after 4 weeks.

The flow properties of β-GPA are sub-optimal. The bulk density is 0.389 g/cc and the tapped density is 0.627 g/cc. These measurements can be used to calculate the Carr's index and Hausner ratio for a substance. The Carr's index and Hausner ratio are indicators of flowability of a powder. As known in the art, e.g., as described in Carr R. L. Chem. Eng. 1965, 72, 163-168, the relationship to flowability of a powder to the Carr's index and Hausner ratio is based on the scale shown in Table 5 below.

TABLE 5

Prediction of powder flowability based on Carr's index and Hausner ratio values

| Carr's Index | Flow character | Hausner Ratio |
|---|---|---|
| 1-10 | Excellent | 1.00-1.11 |
| 11-15 | Good | 1.12-1.18 |
| 16-20 | Fair | 1.19-1.25 |
| 21-25 | Passable | 1.26-1.34 |
| 26-31 | Poor | 1.35-1.45 |
| 32-37 | Very poor | 1.46-1.59 |
| >38 | Very very poor | >1.60 |

The Carr's index and Hausner ratio for β-GPA are 37.9 (Very poor) and 1.610 (Very very poor) respectively. Experiments utilizing a Hanson Flodex instrument confirmed the poor flowability of β-GPA predicted by the Carr's index and Hausner ratio. Thus, there exists a need to find a β-GPA salt with improved physical properties.

Salts

Seventy-six salt screening experiments were carried out with 19 different counterions in different solvent systems including ethanol:water (9:1), isopropyl alcohol, acetone:water (9:1), and acetonitrile. The ten counterions that were prepared in crystalline form were salts prepared with hydrochloric acid, phosphoric acid, methanesulfonic acid, maleic acid, fumaric acid, L-malic acid, succinic acid, and oxalic acid. All of the experiments with basic compounds, e.g., L-aspartic acid, sodium hydroxide, potassium hydroxide, or magnesium hydroxide, resulted in isolation of only β-GPA or the basic compound individually.

Of the salts that were prepared, the hydrochloric acid, L-malic acid, phosphoric acid, methanesulfonic acid, and ethanesulfonic acid salts were found to be stable in dry conditions, but deliquesced under high humidity conditions. The maleic acid, fumaric acid, succinic acid, and oxalic acid salts were found to be stable in both dry and humid conditions. The maleic acid, fumaric acid, and oxalic acid salts were found to have 1:1 (β-GPA:acid) stoichiometry, whereas the succinic acid salt was found to have 2:1 (β-GPA:acid) stoichiometry. Further experiments to generate 2:1 salts with fumaric, oxalic, and maleic acid were conducted, resulting in the preparation of 2:1 salts with maleic acid and fumaric acid.

Dynamic vapor sorption experiments were conducted on the 1:1 maleate salt, the 1:1 fumarate salt, the 2:1 succinate salt, and the 1:1 oxalate salt. The fumarate, succinate, and oxalate salts were found to exhibit less than 1% moisture uptake during the DVS experiment with no form change observed by XRPD after the experiment. The maleate salt exhibited ~25% moisture uptake with no form change observed by XRPD after the experiment. Solid form stability studies of the fumarate, succinate, and oxalate salts were carried out at 40° C. and 75% humidity for seven days. All three salts were found to be stable under these conditions.

The bulk density and tapped density for the three salts was determined as shown in Table 6 below.

TABLE 6

Bulk density and tapped density measurements

| Salt | Bulk density | Tapped density |
| --- | --- | --- |
| oxalate (1:1) | 0.505 g/cc | 0.623 g/cc |
| succinate (2:1) | 0.405 g/cc | 0.472 g/cc |
| fumarate (1:1) | 0.576 g/cc | 0.613 g/cc |

The Carr's index and Hausner ratios were calculated for each of the three salts, and as shown in Table 7, the three salts exhibit greatly improved predicted flow properties compared to β-GPA. The predicted flow properties were confirmed by experiments utilizing a Hanson Flodex instrument.

TABLE 7

Flow properties of three β-GPA salts compared to β-GPA

| Compound | Carr's index | Hausner ratio | Flow character |
| --- | --- | --- | --- |
| β-GPA | 37.9 | 1.610 | Very poor |
| β-GPA oxalate (1:1) | 18.7 | 1.23 | Fair |
| β-GPA succinate (2:1) | 14.3 | 1.167 | Good |
| β-GPA fumarate (1:1) | 5.9 | 1.063 | Excellent |

Polymorph screening of the 1:1 fumarate salt of β-GPA was carried out in 15 different solvent systems at 15° C. and 45° C. and the solubility of the salt was determined gravimetrically. Most of the experiments resulted in no change in polymorph. However, the 2:1 fumarate salt of β-GPA was formed upon lyophilization of the 1:1 salt and fast evaporation, or lyophilization of β-GPA and fumaric acid in 2:1 (β-GPA:acid) stiochiometry. The crystalline form of the 2:1 salt was found to contain some amorphous material, and was unstable. The 2:1 fumarate salt converted to the 1:1 salt when slurried in water, heated, or under high humidity conditions.

Crystalline β-GPA, or a pharmaceutically acceptable salt thereof, is defined as a solid comprising β-GPA, or a pharmaceutically acceptable salt thereof, in which the constituent molecules are packed in a regularly ordered repeating pattern extending in all three spatial dimensions. Identification of crystallinity is readily accomplished in a number of ways known to those skilled in the art. Microscopic examination of a test composition will reveal the presence of regular shapes suggesting ordered internal structure, e.g., the 1:1 fumarate salt of β-GPA produced in Example 1 has rod-like morphology.

XRPD is another method for identifying crystalline β-GPA, or pharmaceutically acceptable salts thereof. The regularly ordered structure of constituent molecules in crystal diffracts incident X-rays in a distinct pattern depicted as a spectrum of peaks. This pattern of peaks for the 1:1 fumarate salt of β-GPA is shown in FIG. 1. While the XRPD peaks for a particular crystal may vary in intensity, the same general pattern will be present in replicate XRPD analysis.

Crystalline 1:1 fumarate salt of β-GPA exhibits an XRPD dominant peak at about 27 2θ(°), ordinarily about 26.7. By "about," as used herein, is meant within the typical variation in measurement of XRPD peaks. Such variations may result from the use of different instruments, instrument settings, batches of product, post-crystallization processing such as micronization or milling, and with varying sample preparation methods. In general, about means±0.5 2θ (°).

Illustrative examples of other dominant peaks for crystalline 1:1 fumarate salt of β-GPA are at about 19, 20, 21, 23, and 29 2θ (°), ordinarily 19.2, 19.7, 20.6, 22.9, and 28.8 2θ (°). Representative peaks for crystalline 1:1 fumarate salt of β-GPA are shown in Table 1.

The identification of a crystalline form of β-GPA, or a pharmaceutically acceptable salt thereof, need not require the presence of any one or more of the dominant peaks seen in FIG. 1 or listed in Table 1. The presence or absence of dominant peaks is ordinarily taken into account with other diagnostic characteristics, e.g., DSC thermogram or TGA graph, to identify a candidate as a particular crystalline form of β-GPA, or a pharmaceutically acceptable salt thereof.

Crystalline 1:1 fumarate salt of β-GPA is also characterized by DSC thermogram which reveals an endothermic onset at 171° C. in differential scanning calorimetry profile. Typically, some variation in this measurement also will be encountered (e.g., ±1-3° C.).

Crystalline 1:1 fumarate salt of β-GPA may also be characterized by thermal gravimetric analysis, e.g., by a loss of weight from 31° C. to 140° C. of less than 1%.

Treatment Methods

β-GPA has recently been found to be effective for the suppression of metastasis. The mechanism of action has been hypothesized as inhibition of creatine transport and/or creatine kinase. The phosphocreatine system promotes metastasis by enhancing the survival of disseminated cancer cells in the liver by acting as an energetic store for ATP generation to endure hepatic hypoxia. Inhibition of creatine transport into cancer cells limits the amount of phosphocreatine available to use in the production of ATP. Inhibition of creatine kinase inhibits the production of ATP through conversion of phosphocreatine to creatine.

Typical vascularized tumors that can be treated with the method include solid tumors, particularly carcinomas, which require a vascular component for the provision of oxygen and nutrients. Exemplary solid tumors include, but are not limited to, carcinomas of the lung, breast, bone, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, Kaposi's sarcoma, and sarcomas.

Treating cancer can result in a reduction in size or volume of a tumor. For example, after treatment, tumor size is reduced by 5% or greater (e.g., 10%, 20%, 30%, 40%, 50%, 60%, 70%, 80%, 90% or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90% or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with a pharmaceutically acceptable salt of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of the invention. A decrease in the mortality rate of a population may also be measured, for example, by calculating for a population the average number of disease-related deaths per unit time following completion of a first round of treatment with a pharmaceutically acceptable salt of the invention.

Compositions

Within the scope of this invention is a composition that contains a suitable excipient and one or more of the pharmaceutically acceptable salts described above. The composition can be a pharmaceutical composition that contains a pharmaceutically acceptable excipient, a dietary composition that contains a dietarily acceptable suitable excipient, or a cosmetic composition that contains a cosmetically acceptable excipient.

The term "pharmaceutical composition" refers to the combination of an active agent with a excipient, inert or active, making the composition especially suitable for diagnostic or therapeutic use in vivo or ex vivo. A "pharmaceutically acceptable excipient," after administered to or upon a subject, does not cause undesirable physiological effects. The excipient in the pharmaceutical composition must be "acceptable" also in the sense that it is compatible with the active ingredient and can be capable of stabilizing it. One or more solubilizing agents can be utilized as pharmaceutical excipients for delivery of an active compound. Examples of a pharmaceutically acceptable excipient include, but are not limited to, biocompatible vehicles, adjuvants, additives, and diluents to achieve a composition usable as a dosage form. Examples of other excipients include colloidal silicon oxide, magnesium stearate, cellulose, sodium lauryl sulfate, and D&C Yellow #10.

As used herein, the term "pharmaceutically acceptable salt" refers to those salts which are, within the scope of sound medical judgment, suitable for use in contact with the tissues of humans and lower animals without undue toxicity, irritation, or allergic response, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66:1-19 (1977). The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, fumaric, or malonic acid or by using other methods used in the art such as ion exchange. Other pharmaceutically acceptable salts, include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Representative alkali or alkaline earth metal salts include sodium, lithium, potassium, calcium, and magnesium. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutical compositions of the present invention additionally include a pharmaceutically acceptable excipient, which, as used herein, includes any and all solvents, diluents, or other liquid vehicle, dispersion or suspension aids, surface active agents, isotonic agents, thickening or emulsifying agents, preservatives, solid binders, and lubricants, as suited to the particular dosage form desired. Remington's Pharmaceutical Sciences, Sixteenth Edition, E. W. Martin (Mack Publishing Co., Easton, Pa., 1980) discloses various excipients used in formulating pharmaceutical compositions and known techniques for the preparation thereof. Except insofar as any conventional excipient medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable excipients include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; natural and synthetic phospholipids, such as soybean and egg yolk phosphatides, lecithin, hydrogenated soy lecithin, dimyristoyl lecithin, dipalmitoyl lecithin, distearoyl lecithin, dioleoyl lecithin, hydroxylated lecithin, lysophosphatidylcholine, cardiolipin, sphingomyelin, phosphatidylcholine, phosphatidyl ethanolamine, diastearoyl phosphatidylethanolamine (DSPE) and its pegylated esters, such as DSPE-PEG750 and, DSPE-PEG2000, phosphatidic acid, phosphatidyl glycerol and phosphatidyl serine. Commercial grades of lecithin which are preferred include those which are available under the trade name Phosal® or Phospholipon® and include Phosal 53 MCT, Phosal 50 PG, Phosal 75 SA, Phospholipon 90H, Phospholipon 90G and Phospholipon 90 NG; soy-phosphatidylcholine (SoyPC) and DSPE-PEG2000 are particularly preferred; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The above-described composition, in any of the forms described above, can be used for treating cancer, or any other disease or condition described herein. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment. A pharmaceutical composition of this invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acids, such as, but not limited to, oleic acid and its glyceride derivatives, are useful in the preparation of injectables, as are natural pharmaceutically acceptable oils, such as, but not limited to, olive oil or castor oil, orpolyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used excipients include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Pharmaceutical compositions for topical administration according to the described invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally include one or more excipients or diluents. In some preferred embodiments, the topical formulations include a material that would enhance absorption or penetration of the active agent(s) through the skin or other affected areas.

A topical composition contains a safe and effective amount of a dermatologically acceptable excipient suitable for application to the skin. A "cosmetically acceptable" or "dermatologically-acceptable" composition or component refers a composition or component that is suitable for use in contact with human skin without undue toxicity, incompatibility, instability, or allergic response. The excipient enables an active agent and optional component to be delivered to the skin at an appropriate concentration(s). The excipient thus can act as a diluent, dispersant, solvent, or the like to ensure that the active materials are applied to and distributed evenly over the selected target at an appropriate concentration. The excipient can be solid, semi-solid, or liquid. The excipient can be in the form of a lotion, a cream, or a gel, in particular one that has a sufficient thickness or yield point to prevent the active materials from sedimenting. The excipient can be inert or possess dermatological benefits. It also should be physically and chemically compatible with the active components described herein, and should not unduly impair stability, efficacy, or other use benefits associated with the composition.

Combination Therapies

In some embodiments, the pharmaceutical composition may further include an additional compound having antiproliferative activity. The additional compound having antiproliferative activity can be selected from a group of antiproliferative agents including those shown in Table 8.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

By "antiproliferative agent" is meant any antiproliferative agent, including those antiproliferative agents listed in Table 8, any of which can be used in combination with a pharmaceutically acceptable salt of the invention to treat the medical conditions recited herein. Antiproliferative agents also include organo-platine derivatives, naphtoquinone and benzoquinone derivatives, chrysophanic acid and anthroquinone derivatives thereof.

TABLE 8

| | | |
|---|---|---|
| Alkylating agents | Busulfan | Chlorambucil |
| | dacarbazine | procarbazine |
| | ifosfamide | altretamine |
| | hexamethylmelamine | estramustine phosphate |
| | thiotepa | mechlorethamine |
| | dacarbazine | streptozocin |
| | lomustine | temozolomide |
| | cyclophosphamide | Semustine |
| Platinum agents | spiroplatin | lobaplatin (Aeterna) |
| | tetraplatin | satraplatin (Johnson Matthey) |
| | ormaplatin | BBR-3464 (Hoffmann-La Roche |
| | iproplatin | SM-11355 (Sumitomo) |
| | ZD-0473 (AnorMED) | AP-5280 (Access) |
| | oxaliplatin | cisplatin |
| | carboplatin | |
| Antimetabolites | azacytidine | trimetrexate |
| | Floxuridine | deoxycoformycin |
| | 2-chlorodeoxyadenosine | pentostatin |
| | 6-mercaptopurine | hydroxyurea |
| | 6-thioguanine | decitabine (SuperGen) |
| | cytarabine | clofarabine (Bioenvision) |
| | 2-fluorodeoxy cytidine | irofulven (MGI Pharma) |
| | methotrexate | DMDC (Hoffmann-La Roche) |
| | tomudex | ethynylcytidine (Taiho) |
| | fludarabine | gemcitabine |
| | raltitrexed | capecitabine |
| Topoisomerase inhibitors | amsacrine | exatecan mesylate (Daiichi) |
| | epirubicin | quinamed (ChemGenex) |
| | etoposide | gimatecan (Sigma-Tau) |
| | teniposide or mitoxantrone | diflomotecan (Beaufour-Ipsen) |
| | 7-ethyl-10-hydroxy-camptothecin | TAS-103 (Taiho) |
| | dexrazoxanet (TopoTarget) | elsamitrucin (Spectrum) |
| | pixantrone (Novuspharma) | J-107088 (Merck & Co) |
| | rebeccamycin analogue (Exelixis) | BNP-1350 (BioNumerik) |
| | BBR-3576 (Novuspharma) | CKD-602 (Chong Kun Dang) |
| | rubitecan (SuperGen) | KW-2170 (Kyowa Hakko) |
| | irinotecan (CPT-11) | hydroxycamptothecin (SN-38) |
| | topotecan | |
| Antitumor antibiotics | valrubicin | azonafide |
| | therarubicin | anthrapyrazole |
| | idarubicin | oxantrazole |
| | rubidazone | losoxantrone |
| | plicamycin | MEN-10755 (Menarini) |
| | porfiromycin | GPX-100 (Gem Pharmaceuticals) |
| | mitoxantrone (novantrone) | Epirubicin |
| | amonafide | mitoxantrone |
| | | doxorubicin |
| Antimitotic agents | colchicine | E7010 (Abbott) |
| | vinblastine | PG-TXL (Cell Therapeutics) |
| | vindesine | IDN 5109 (Bayer) |
| | dolastatin 10 (NCI) | A 105972 (Abbott) |
| | rhizoxin (Fujisawa) | A 204197 (Abbott) |
| | mivobulin (Warner-Lambert) | LU 223651 (BASF) |
| | cemadotin (BASF) | D 24851 (ASTAMedica) |
| | RPR 109881A (Aventis) | ER-86526 (Eisai) |
| | TXD 258 (Aventis) | combretastatin A4 (BMS) |
| | epothilone B (Novartis) | isohomohalichondrin-B (PharmaMar) |
| | T 900607 (Tularik) | ZD 6126 (AstraZeneca) |
| | T 138067 (Tularik) | AZ10992 (Asahi) |
| | cryptophycin 52 (Eli Lilly) | IDN-5109 (Indena) |
| | vinflunine (Fabre) | AVLB (Prescient NeuroPharma) |
| | auristatin PE (Teikoku Hormone) | azaepothilone B (BMS) |
| | BMS 247550 (BMS) | BNP-7787 (BioNumerik) |
| | BMS 184476 (BMS) | CA-4 prodrug (OXiGENE) |
| | BMS 188797 (BMS) | dolastatin-10 (NIH) |
| | taxoprexin (Protarga) | CA-4 (OXiGENE) |
| | SB 408075 (GlaxoSmithKline) | docetaxel |
| | Vinorelbine | vincristine |
| | Trichostatin A | paclitaxel |
| Aromatase inhibitors | aminoglutethimide | YM-511 (Yamanouchi) |
| | atamestane (BioMedicines) | formestane |
| | letrozole | exemestane |
| | anastrazole | |

TABLE 8-continued

| | | | |
|---|---|---|---|
| Thymidylate synthase inhibitors | pemetrexed (Eli Lilly) ZD-9331 (BTG) | | nolatrexed (Eximias) CoFactor ™ (BioKeys) |
| DNA antagonists | trabectedin (PharmaMar) glufosfamide (Baxter International) albumin + 32P (Isotope Solutions) thymectacin (NewBiotics) | | edotreotide (Novartis) mafosfamide (Baxter International) apaziquone (Spectrum Pharmaceuticals) O6 benzyl guanine (Paligent) |
| Farnesyltransferase inhibitors | arglabin (NuOncology Labs) lonafarnib (Schering-Plough) BAY-43-9006 (Bayer) | | tipifarnib (Johnson & Johnson) perillyl alcohol (DOR BioPharma) |
| Pump inhibitors | CBT-1 (CBA Pharma) tariquidar (Xenova) MS-209 (Schering AG) | | zosuquidar trihydrochloride (Eli Lilly) biricodar dicitrate (Vertex) |
| Histone acetyltransferase inhibitors | tacedinaline (Pfizer) SAHA (Aton Pharma) MS-275 (Schering AG) | | pivaloyloxymethyl butyrate (Titan) depsipeptide (Fujisawa) |
| Metalloproteinase inhibitors | Neovastat (Aeterna Laboratories) marimastat (British Biotech) | | CMT-3 (CollaGenex) BMS-275291 (Celltech) |
| Ribonucleoside reductase inhibitors | gallium maltolate (Titan) triapine (Vion) | | tezacitabine (Aventis) didox (Molecules for Health) |
| TNF alpha agonists/antagonists | virulizin (Lorus Therapeutics) CDC-394 (Celgene) | | revimid (Celgene) |
| Endothelin A receptor antagonist | atrasentan (Abbott) ZD-4054 (AstraZeneca) | | YM-598 (Yamanouchi) |
| Retinoic acid receptor agonists | fenretinide (Johnson & Johnson) LGD-1550 (Ligand) | | alitretinoin (Ligand) |
| Immuno-modulators | interferon oncophage (Antigenics) GMK (Progenics) adenocarcinoma vaccine (Biomira) CTP-37 (AVI BioPharma) IRX-2 (Immuno-Rx) PEP-005 (Peplin Biotech) synchrovax vaccines (CTL Immuno) melanoma vaccine (CTL Immuno) p21 RAS vaccine (GemVax) MAGE-A3 (GSK) nivolumab (BMS) abatacept (BMS) pembrolizumab | | dexosome therapy (Anosys) pentrix (Australian Cancer Technology) ISF-154 (Tragen) cancer vaccine (Intercell) norelin (Biostar) BLP-25 (Biomira) MGV (Progenics) β-alethine (Dovetail) CLL therapy (Vasogen) Ipilimumab (BMS), CM-10 (cCam Biotherapeutics) MPDL3280A (Genentech) MEDI4736 |
| Hormonal and antihormonal agents | estrogens conjugated estrogens ethinyl estradiol chlortrianisen idenestrol hydroxyprogesterone caproate medroxyprogesterone testosterone testosterone propionate; fluoxymesterone methyltestosterone diethylstilbestrol megestrol bicalutamide flutamide nilutamide | | dexamethasone prednisone methylprednisolone prednisolone aminoglutethimide leuprolide octreotide mitotane P-04 (Novogen) 2-methoxyestradiol (EntreMed) arzoxifene (Eli Lilly) tamoxifen toremofine goserelin Leuporelin bicalutamide |
| Photodynamic agents | talaporfin (Light Sciences) Theralux (Theratechnologies) motexafin gadolinium (Pharmacyclics) | | Pd-bacteriopheophorbide (Yeda) lutetium texaphyrin (Pharmacyclics) hypericin |
| Kinase Inhibitors | imatinib (Novartis) leflunomide (Sugen/Pharmacia) ZD1839 (AstraZeneca) erlotinib (Oncogene Science) canertinib (Pfizer) squalamine (Genaera) SU5416 (Pharmacia) SU6668 (Pharmacia) ZD4190 (AstraZeneca) ZD6474 (AstraZeneca) vatalanib (Novartis) PKI166 (Novartis) GW2016 (GlaxoSmithKline) EKB-509 (Wyeth) trastuzumab (Genentech) OSI-774 (Tarceva ™) CI-1033 (Pfizer) SU11248 (Pharmacia) RH3 (York Medical) Genistein | | EKB-569 (Wyeth) kahalide F (PharmaMar) CEP-701 (Cephalon) CEP-751 (Cephalon) MLN518 (Millenium) PKC412 (Novartis) Phenoxodiol (Novogen) C225 (ImClone) rhu-Mab (Genentech) MDX-H210 (Medarex) 2C4 (Genentech) MDX-447 (Medarex) ABX-EGF (Abgenix) IMC-1C11 (ImClone) Tyrphostins Gefitinib (Iressa) PTK787 (Novartis) EMD 72000 (Merck) Emodin Radicinol |

TABLE 8-continued

| | |
|---|---|
| Radicinol | Vemurafenib (B-Raf enzyme |
| Met-MAb (Roche) | inhibitor, Daiichi Sankyo) |
| SR-27897 (CCK A inhibitor, Sanofi-Synthelabo) | ceflatonin (apoptosis promotor, ChemGenex) |
| tocladesine (cyclic AMP agonist, Ribapharm) | BCX-1777 (PNP inhibitor, BioCryst) |
| alvocidib (CDK inhibitor, Aventis) | ranpirnase (ribonuclease stimulant, Alfacell) |
| CV-247 (COX-2 inhibitor, Ivy Medical) | galarubicin (RNA synthesis inhibitor, Dong-A) |
| P54 (COX-2 inhibitor, Phytopharm) | tirapazamine (reducing agent, SRI |
| CapCell ™ (CYP450 stimulant, Bavarian Nordic) | International) |
| GCS-100 (gal3 antagonist, GlycoGenesys) | N-acetylcysteine (reducing agent, Zambon) |
| G17DT immunogen (gastrin inhibitor, Aphton) | R-flurbiprofen (NF-kappaB inhibitor, Encore) |
| efaproxiral (oxygenator, Allos Therapeutics) | 3CPA (NF-kappaB inhibitor, Active Biotech) |
| PI-88 (heparanase inhibitor, Progen) | seocalcitol (vitamin D receptor agonist, Leo) |
| tesmilifene (histamine antagonist, YM BioSciences) | 131-I-TM-601 (DNA antagonist, TransMolecular) |
| histamine (histamine H2 receptor agonist, Maxim) | eflornithine (ODC inhibitor, ILEX Oncology) |
| tiazofurin (IMPDH inhibitor, Ribapharm) | minodronic acid (osteoclast inhibitor, Yamanouchi) |
| cilengitide (integrin antagonist, Merck KGaA) | |
| SR-31747 (IL-1 antagonist, Sanofi-Synthelabo) | indisulam (p53 stimulant, Eisai) |
| CCI-779 (mTOR kinase inhibitor, Wyeth) | aplidine (PPT inhibitor, PharmaMar) |
| exisulind (PDE V inhibitor, Cell Pathways) | gemtuzumab (CD33 antibody, Wyeth Ayerst) |
| CP-461 (PDE V inhibitor, Cell Pathways) | PG2 (hematopoiesis enhancer, Pharmagenesis) |
| AG-2037 (GART inhibitor, Pfizer) | |
| WX-UK1 (plasminogen activator inhibitor, Wilex) | Immunol ™ (triclosan oral rinse, Endo) |
| PBI-1402 (PMN stimulant, ProMetic LifeSciences) | triacetyluridine (uridine prodrug, Wellstat) |
| bortezomib (proteasome inhibitor, Millennium) | SN-4071 (sarcoma agent, Signature BioScience) |
| SRL-172 (T cell stimulant, SR Pharma) | |
| TLK-286 (glutathione S transferase inhibitor, Telik) | TransMID-107 ™ (immunotoxin, KS Biomedix) |
| | PCK-3145 (apoptosis promotor, Procyon) |
| PT-100 (growth factor agonist, Point Therapeutics) | doranidazole (apoptosis promotor, Pola) |
| | cafestol |
| Chrysophanic acid | kahweol |
| Cesium oxides | caffeic acid |
| BRAF inhibitors, | Tyrphostin AG |
| PDL1 inhibitors | PD-1 inhibitors |
| MEK inhibitors | CTLA-4 inhibitors |
| bevacizumab | brostallicin (apoptosis promotor, Pharmacia) |
| angiogenesis inhibitors | β-lapachone |
| Absinthin | gelonin |
| dabrafenib | CRS-207 |
| midostaurin (PKC inhibitor, Novartis) | CHS-828 (cytotoxic agent, Leo) |
| bryostatin-1 (PKC stimulant, GPC Biotech) | trans-retinoic acid (differentiator, NIH) |
| CDA-II (apoptosis promotor, Everlife) | MX6 (apoptosis promotor, MAXIA) |
| SDX-101 (apoptosis promotor, Salmedix) | apomine (apoptosis promotor, ILEX Oncology) |
| rituximab (CD20 antibody, Genentech) | sorafenib |
| carmustine | BRAF inhibitors |
| Mitoxantrone | urocidin (apoptosis promotor, Bioniche) |
| Bleomycin | Ro-31-7453 (apoptosis promotor, La Roche) |

EXAMPLES

General Methods

Differential Scanning Calorimetry

Differential Scanning calorimetry (DCS) data were collected using a TA Instruments Q10 DSC. Typically, samples (2-8 mg) were placed in unsealed, but covered hermetic alodined aluminum sample pans and scanned from 30 to 300° C. at a rate of 10° C./min using a nitrogen purge of 50 mL/min.

Thermal Gravimetric Analysis

Thermal Gravimetric Analysis (TGA) data were collected using a TA Instruments TGA Q500. Typically, samples (~10 mg) were placed in an open, pre-tared aluminum sample pan and scanned from 25 to 300° C. at a rate of 10° C./min using a nitrogen purge at 60 mL/min.

X-ray Powder Diffractometer

X-ray powder diffraction patterns were obtained using a Bruker D8 Advance equipped with a Cu Kα radiation source ($\lambda$=1.54° A), a 9-position sample holder and a LYNXEYE super speed detector. Samples were placed on zero-background, silicon plate holders.

Dynamic Vapor Sorption

Samples were analyzed using an Aquadyne DVS-2 gravimetric water sorption analyzer. The relative humidity was adjusted between 2-95% and the weight of the sample was continuously monitored and recorded.

Proton-Nuclear Magnetic Resonance

Sample was prepared by dissolving the compound in deuterated dimethylsulfoxide with 0.05% (v/v) tetramethylsilane (TMS). Spectra were collected at ambient temperature on a Bruker Avance 300 MHz NMR with TopSpin software. The number of scans was 16 for proton NMR.

Karl Fischer

The apparent water content in samples was determined by Karl Fischer titration using a Mettler Toledo DL39 Coulometric KF Titrator. HYDRANAL-Coulomat AD was used as the titrant. About 20 mg of the solid was used for titration. The analytical parameters are presented in Table 9.

TABLE 9

| KF Parameter | Value |
| --- | --- |
| Speed [%] | 40 |
| Mix time [sec] | 10 |
| Auto start | No |
| Blank [µg] | 0 |
| Drift [µg/min] | 5 |
| Calculation | Ug |
| Standby | Yes |

Karl Fischer parameters

TABLE 9-continued

| KF Parameter | Value |
| --- | --- |
| Initial drift [µg/min] | <10 |
| Initial Potential [mV] | 100 |

Karl Fischer parameters

Optical Microscopy

Samples were analyzed using an Olympus BX53 polarized light microscope equipped with a PAXcam 3 digital microscope camera.

Example 1. Profiling of Solid-state β-GPA

Figure 2:
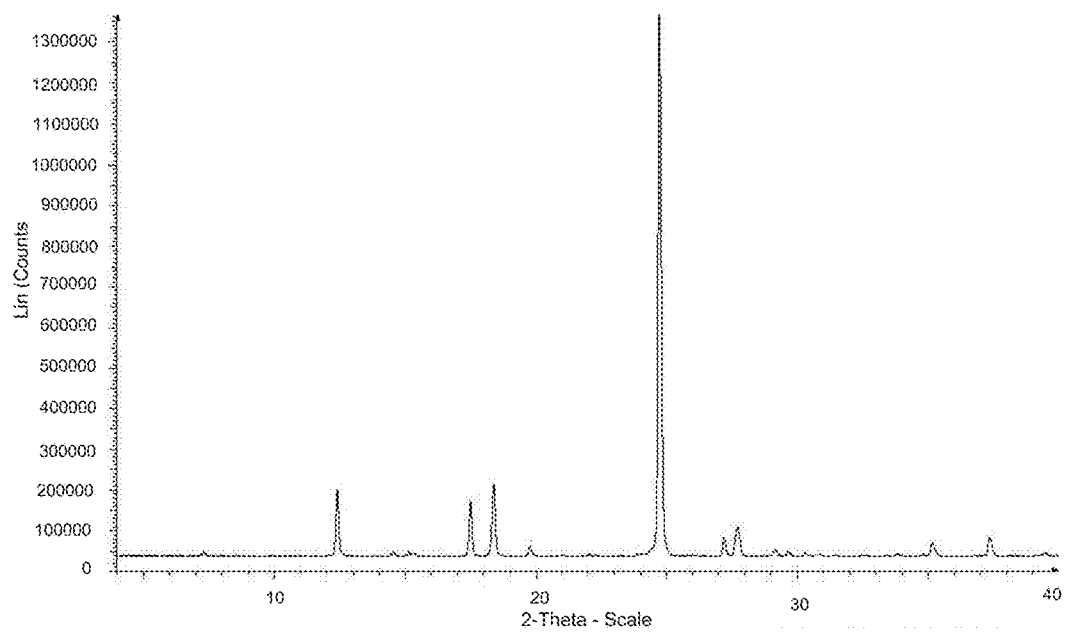
FIG. 2 is an image depicting X-ray powder diffraction (XRPD) pattern obtained for a crystalline form of β-GPA.
Figure 3:
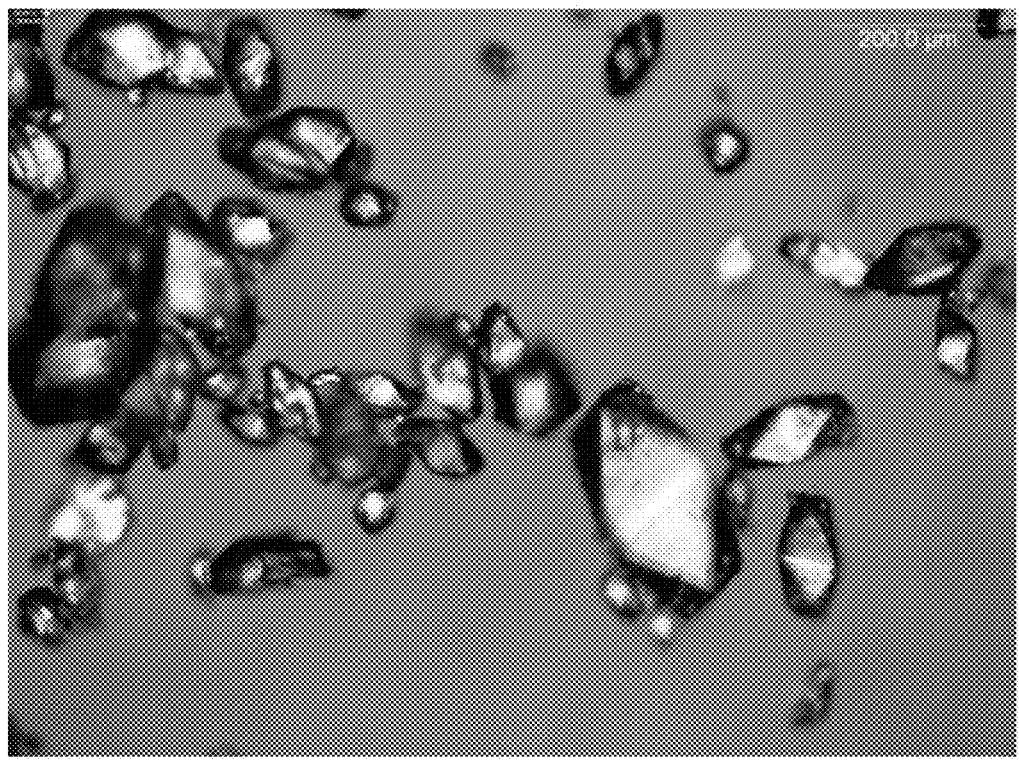
FIG. 3 is an image of β-GPA crystals under a polarized microscope.
Figure 4:
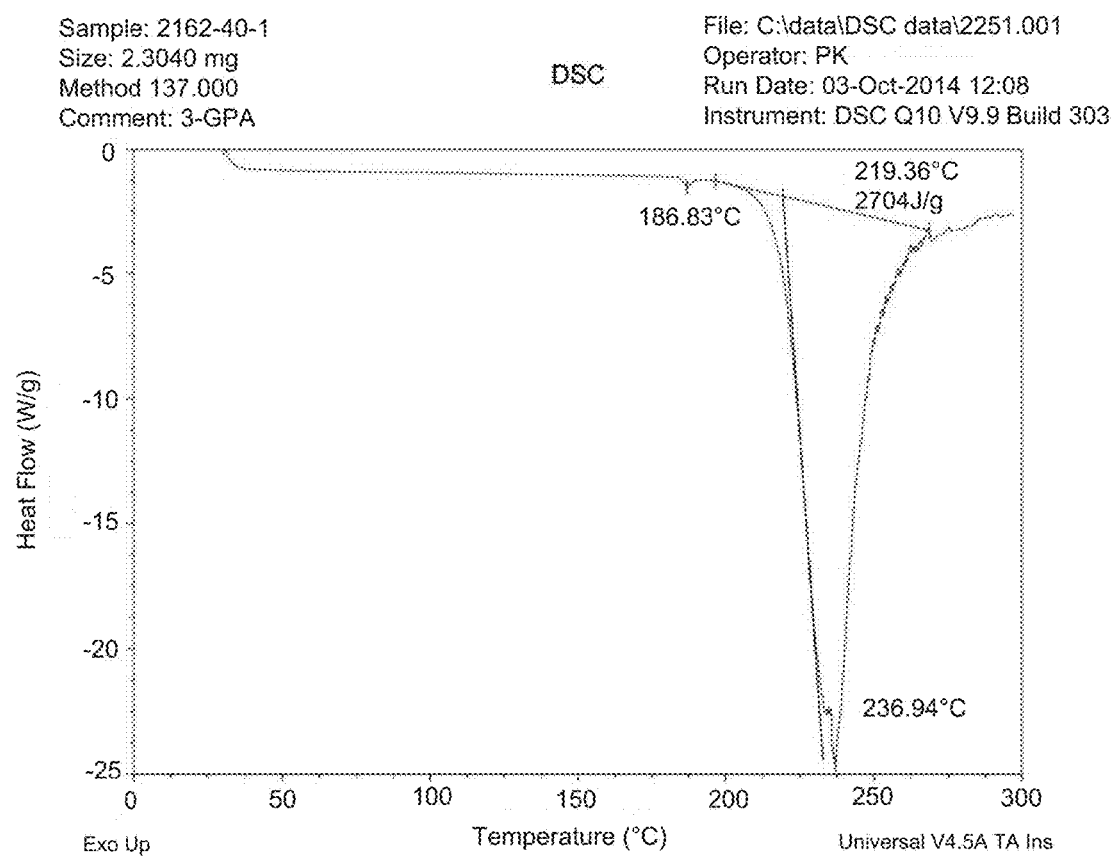
FIG. 4 is an image depicting a DSC thermogram obtained for a crystalline form of β-GPA.

Solid-state β-GPA was analyzed by XRPD (FIG. 2) and was also observed under a polarized microscope (FIG. 3). The material was found to be crystalline A DSC thermogram of β-GPA is illustrated in FIG. 4. The melting onset of β-GPA was found to be around 219° C. followed by an endothermic event at around 237° C. and immediate possible degradation. However, another tiny endothermic event at 187° C. was also exhibited by the material (possible traces of another form of β-GPA).

Figure 5:
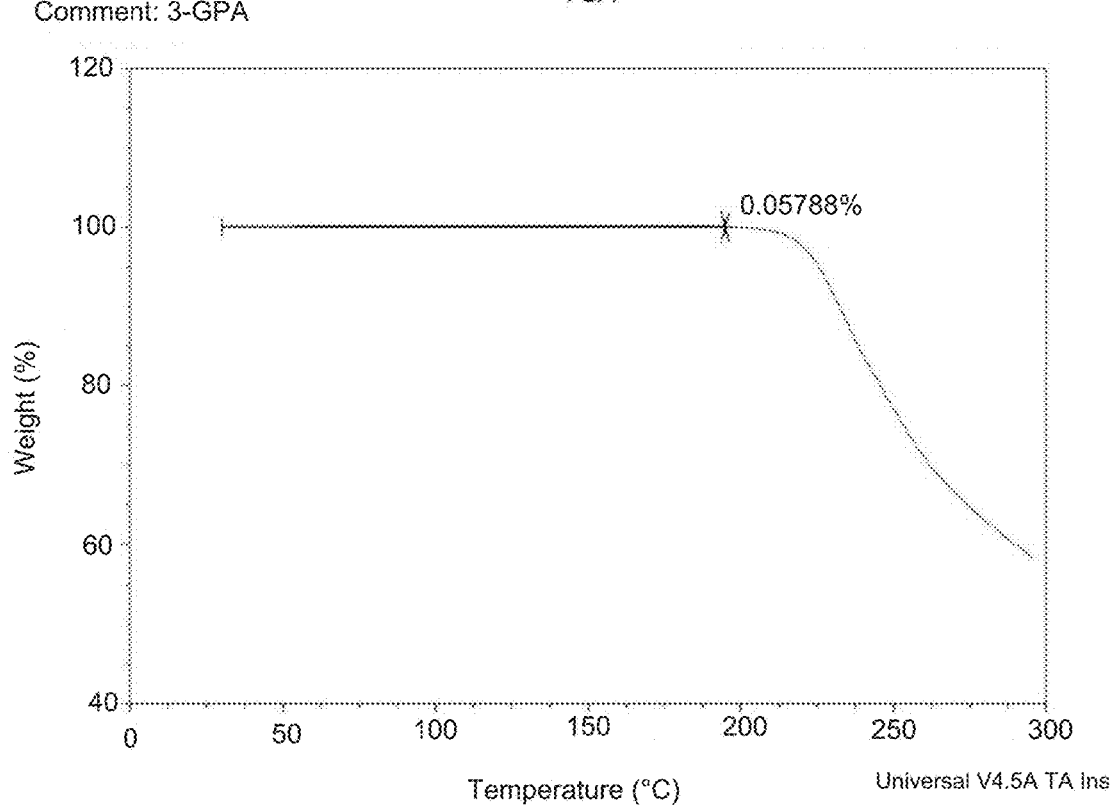
FIG. 5 is an image depicting TGA analysis obtained for a crystalline form of β-GPA.

TGA analysis reveals that there is less than 0.1% weight loss in the sample from 30 to 145° C. as illustrated in FIG. 5.

Figure 6:
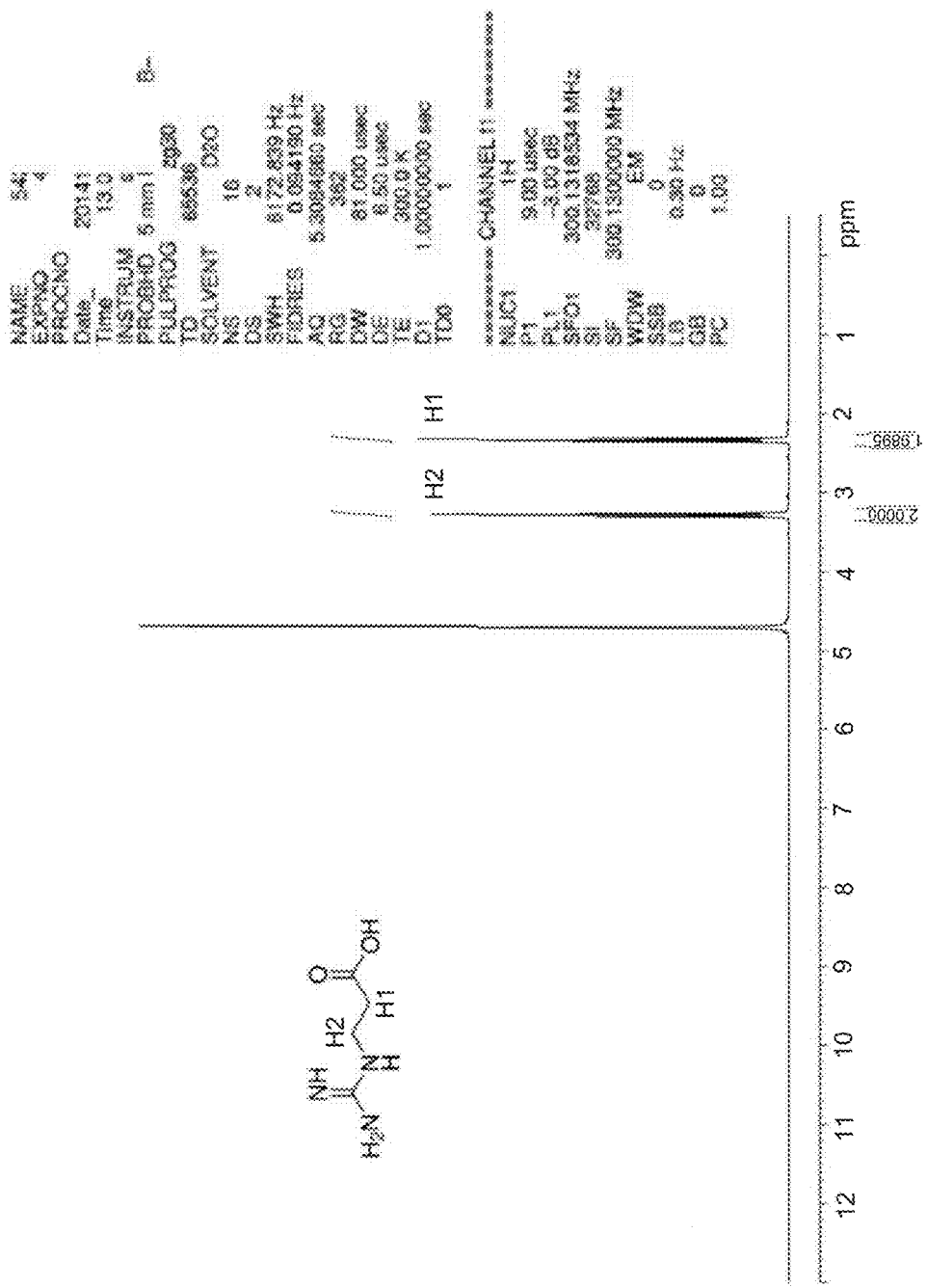
FIG. 6 is an image depicting a $^1$H NMR spectra of a crystalline form β-GPA.

The $^1$H NMR of β-GPA is shown in FIG. 6.

Figure 7:
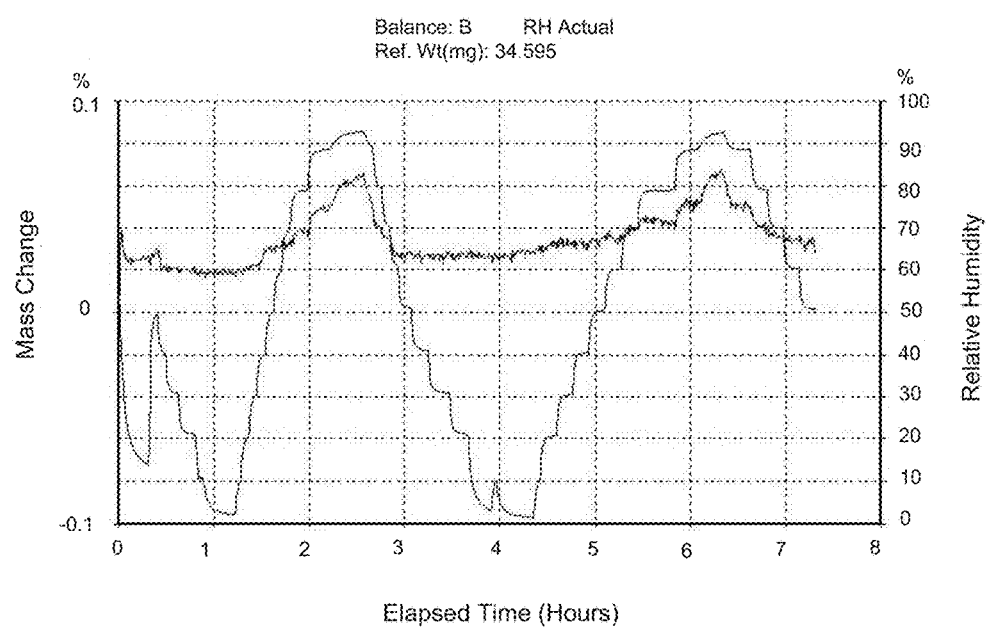
FIG. 7 is an image depicting a DVS analysis for a crystalline form of β-GPA.
Figure 8:
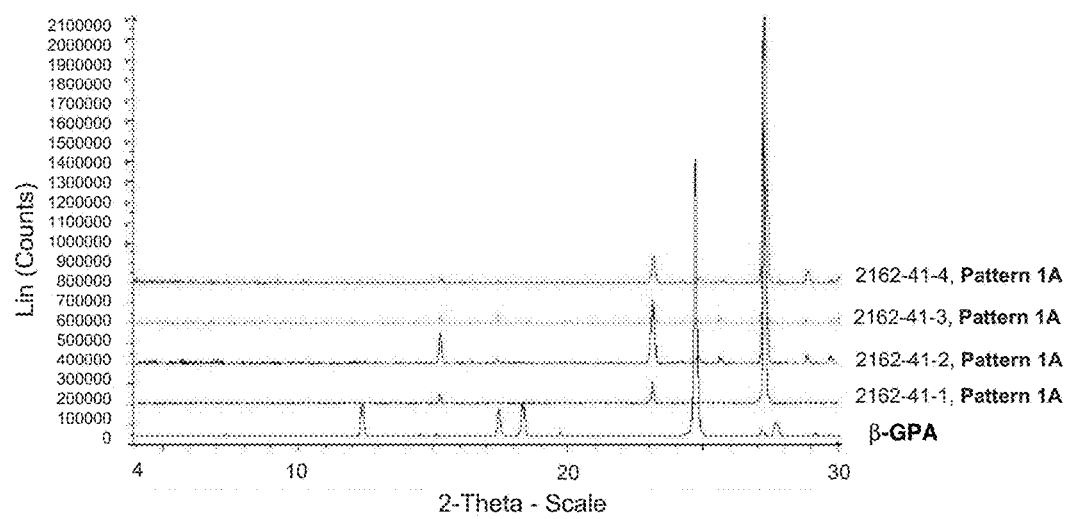
FIG. 8 is an image depicting X-ray powder diffraction (XRPD) pattern obtained for a crystalline form of the 1:1 hydrochloride salt of β-GPA.
Figure 9:
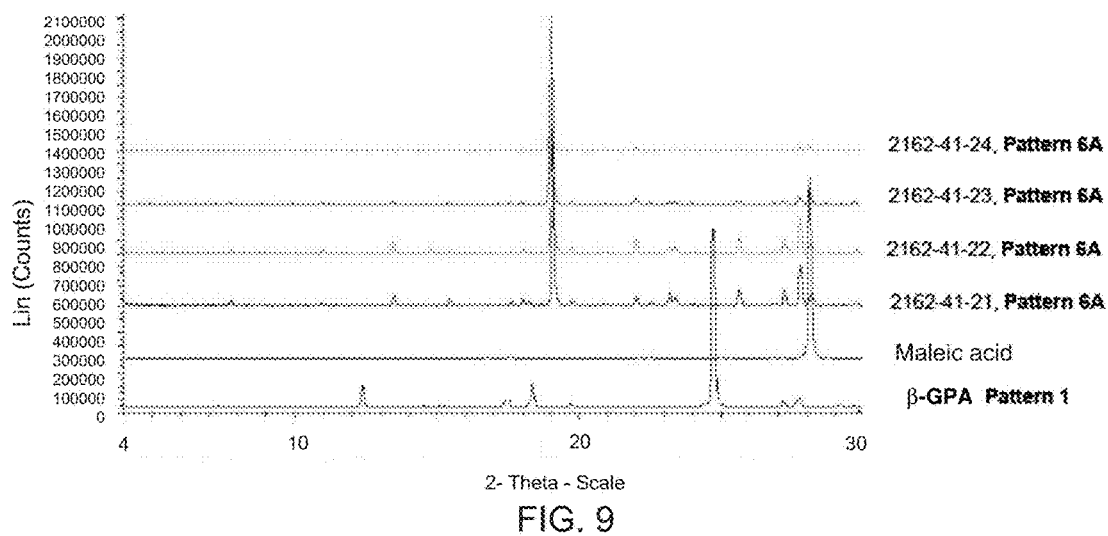
FIG. 9 is an image depicting X-ray powder diffraction (XRPD) pattern obtained for a crystalline form of the 1:1 maleate salt of β-GPA.
Figure 10:
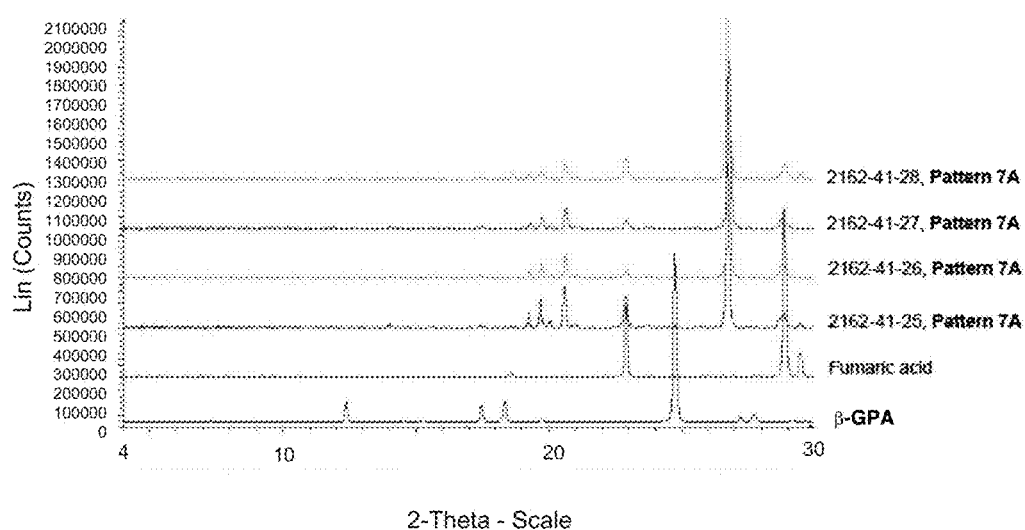
FIG. 10 is an image depicting X-ray powder diffraction (XRPD) pattern obtained for a crystalline form of the 1:1 fumarate salt of β-GPA.
Figure 11:
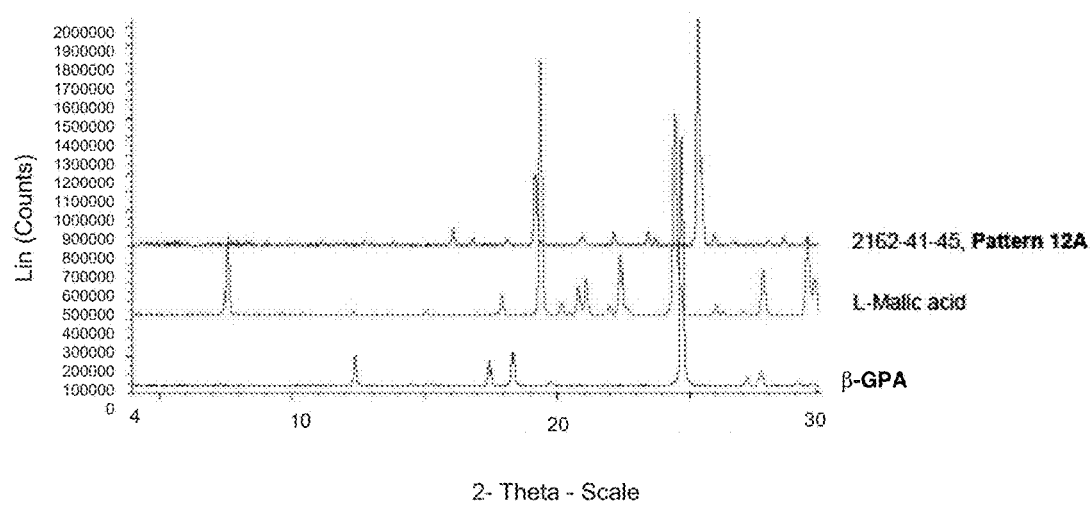
FIG. 11 is an image depicting X-ray powder diffraction (XRPD) pattern obtained for a crystalline form of the 1:1 L-malic acid salt of β-GPA.
Figure 12:
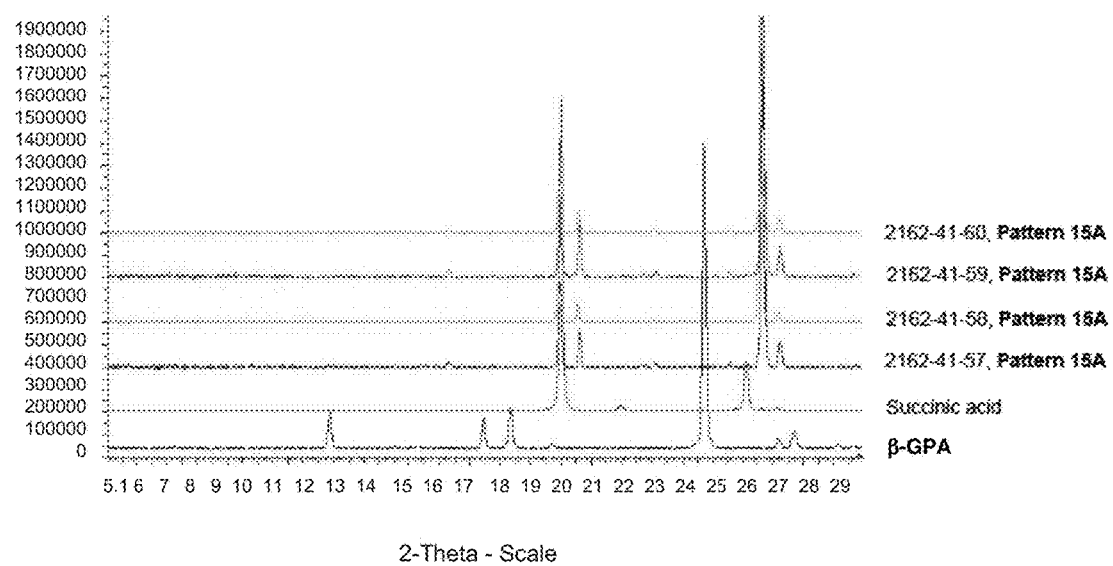
FIG. 12 is an image depicting X-ray powder diffraction (XRPD) pattern obtained for a crystalline form of the 2:1 succinate salt of β-GPA.
Figure 13:
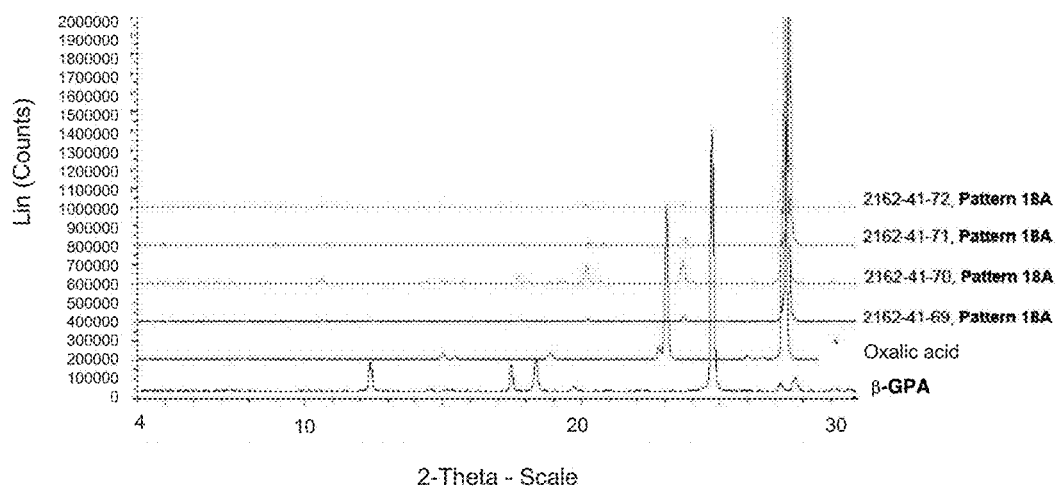
FIG. 13 is an image depicting X-ray powder diffraction (XRPD) pattern obtained for a crystalline form of the 1:1 oxalate salt of β-GPA.

The DVS experiment of β-GPA revealed around 0.1% moisture absorbed and desorbed when exposed to relative humidity between 0-95 percent (FIG. 7). No change in the solid form was observed after the DVS experiment as confirmed by XRPD.

Example 2. Salt Screening

Stage I

Table 10 illustrates the selected counter ions for the salt screening of β-GPA. Salt screening experiments were designed in 1:1.1 equivalence (eq) for β-GPA to counter ion.

TABLE 10

List of selected counterions

| Sample ID | β-GPA (mg) | Counterion | Counterion sequence # | Counterion molecular wt |
| --- | --- | --- | --- | --- |
| 2162-42-1 to 4 | 30 | Hydrochloric acid (36-38%)* | 1 | 36.46 |
| 2162-42-5 to 8 | 30 | Hydrobromic acid (48%)* | 2 | 80.91 |
| 2162-42-9 to 12 | 30 | Sulfuric acid (95-98%)* | 3 | 98.08 |
| 2162-42-13 to 16 | 30 | Phosphoric acid (85%)* | 4 | 98.00 |
| 2162-42-17 to 20 | 30 | Methane sulfonic acid (98%)* | 5 | 96.11 |
| 2162-42-21 to 24 | 30 | Maleic acid | 6 | 116.07 |
| 2162-42-25 to 28 | 30 | Fumaric acid | 7 | 116.07 |
| 2162-42-29 to 32 | 30 | Tartaric acid | 8 | 150.09 |
| 2162-42-33 to 36 | 30 | Ethanesulfonic acid | 9 | 110.13 |
| 2162-42-37 to 40 | 30 | Ethanedisulfonic acid | 10 | 190.20 |
| 2162-42-41 to 44 | 30 | Citric acid | 11 | 192.12 |
| 2162-42-45 to 48 | 30 | Malic acid | 12 | 134.09 |
| 2162-42-49 to 52 | 30 | Lactic acid | 13 | 90.08 |
| 2162-42-53 to 56 | 30 | Aspartic acid | 14 | 133.1 |
| 2162-42-57 to 60 | 30 | Succinic acid | 15 | 118.09 |
| 2162-42-61 to 64 | 30 | Sodium hydroxide | 16 | 40.00 |
| 2162-42-65 to 68 | 30 | Potassium hydroxide | 17 | 56.11 |
| 2162-42-69 to 72 | 30 | Oxalic acid | 18 | 90.03 |
| 2162-45-1 to 4 | 30 | Magnesium hydroxide | 19 | 58.32 |

76 salt screening experiments of β-GPA with 19 different counter ions were set up with 30 mg of β-GPA. Sets of four vials for each counterion were set up with four different solvents (0.3 mL):ethanol:water (9:1), isopropanol, acetone:water (9:1) and acetonitrile.

Appropriate amounts of β-GPA and the counterion were dissolved in the respective solvents and heated to 70-75° C. until dissolved. An additional 0.1 mL of water was added to the samples containing isopropanol, acetone:water (9:1) and acetonitrile. To samples containing L-aspartic acid, around 1.5 mL of water was required to dissolve the solids. After a clear solution was obtained, the samples were left for stirring at room temperature. Solids were observed in the following samples: 2163-42-4, 25, 26, 27, 28, 45 and 53 through 75. The solids were filtered and analyzed by XRPD immediately as wet sample. The samples that did not yield solids were placed in the oven at 50° C. for drying. The following samples resulted in solids after overnight drying: 2162-42-2, 1, 2, 3 and 21 through 24. The experiments with L-aspartic acid, sodium hydroxide, potassium hydroxide, and magnesium hydroxide resulted in the precipitation of either β-GPA or the counterion. All the experimental observations were recorded after every step and are listed in Table 11.

TABLE 11

Results of Salt screening

| Sample ID | Counterion | Solvent | After 24 hours | After Drying | XRPD |
|---|---|---|---|---|---|
| 2162-42-1 | Hydrochloric | EtOH:H$_2$O (9:1) | Clear Solution | White Solid | Pattern 1A |
| 2162-42-2 | Acid | IPA | Clear Solution | White Solid | |
| 2162-42-3 | | Acetone:H$_2$O (9:1) | Clear Solution | White Solid | |
| 2162-42-4 | | MeCN | White Solid | N/A | |
| 2162-42-5 | Hydrobromic | EtOH:H$_2$O (9:1) | Clear Solution | Gel | N/A |
| 2162-42-6 | Acid | IPA | Clear Solution | Gel | N/A |
| 2162-42-7 | | Acetone:H$_2$O (9:1) | Clear Solution | Gel | N/A |
| 2162-42-8 | | MeCN | Clear Solution | Gel | N/A |
| 2162-42-9 | Sulfuric Acid | EtOH:H$_2$O (9:1) | Clear Solution | Gel | N/A |
| 2162-42-10 | | IPA | Clear Solution | Gel | N/A |
| 2162-42-11 | | Acetone:H$_2$O (9:1) | Clear Solution | Gel | N/A |
| 2162-42-12 | | MeCN | Clear Solution | Gel | N/A |
| 2162-42-13 | Phosphoric Acid | EtOH:H$_2$O (9:1) | Clear Solution | Gel | N/A |
| 2162-42-14 | | IPA | Clear Solution | Gel | N/A |
| 2162-42-15 | | Acetone:H$_2$O (9:1) | Clear Solution | Gel | N/A |
| 2162-42-16 | | MeCN | Clear Solution | Gel | N/A |
| 2162-42-17 | Methanesulfonic | EtOH:H$_2$O (9:1) | Clear Solution | Gel | N/A |
| 2162-42-18 | Acid | IPA | Clear Solution | Gel | N/A |
| 2162-42-19 | | Acetone:H$_2$O (9:1) | Clear Solution | Gel | N/A |
| 2162-42-20 | | MeCN | Clear Solution | Gel | N/A |
| 2162-42-21 | Maleic Acid | EtOH:H$_2$O (9:1) | Clear Solution | White Solid | Pattern 6A |
| 2162-42-22 | | IPA | Clear Solution | White Solid | |
| 2162-42-23 | | Acetone:H$_2$O (9:1) | Clear Solution | White Solid | |
| 2162-42-24 | | MeCN | Clear Solution | White Solid | |
| 2162-42-25 | Fumaric Acid | EtOH:H$_2$O (9:1) | White Solid | N/A | Pattern 7A |
| 2162-42-26 | | IPA | White Solid | N/A | |
| 2162-42-27 | | Acetone:H$_2$O (9:1) | White Solid | N/A | |
| 2162-42-28 | | MeCN | White Solid | N/A | |
| 2162-42-29 | L-Tartaric Acid | EtOH:H$_2$O (9:1) | Clear Solution | Gel | N/A |
| 2162-42-30 | | IPA | Clear Solution | Gel | N/A |
| 2162-42-31 | | Acetone:H$_2$O (9:1) | Clear Solution | Gel | N/A |
| 2162-42-32 | | MeCN | Clear Solution | Gel | N/A |
| 2162-42-33 | Ethanesulfonic | EtOH:H$_2$O (9:1) | Clear Solution | Gel | N/A |
| 2162-42-34 | Acid | IPA | Clear Solution | Gel | N/A |
| 2162-42-35 | | Acetone:H$_2$O (9:1) | Clear Solution | Gel | N/A |
| 2162-42-36 | | MeCN | Clear Solution | Gel | N/A |
| 2162-42-37 | Ethanedisulfonic | EtOH:H$_2$O (9:1) | Clear Solution | Gel | N/A |
| 2162-42-38 | Acid | IPA | Clear Solution | Gel | N/A |
| 2162-42-39 | | Acetone:H$_2$O (9:1) | Clear Solution | Gel | N/A |
| 2162-42-40 | | MeCN | Clear Solution | Gel | N/A |
| 2162-42-41 | Citric Acid | EtOH:H$_2$O (9:1) | Clear Solution | Gel | N/A |
| 2162-42-42 | | IPA | Clear Solution | Gel | N/A |
| 2162-42-43 | | Acetone:H$_2$O (9:1) | Clear Solution | Gel | N/A |
| 2162-42-44 | | MeCN | Clear Solution | Gel | N/A |
| 2162-42-45 | L-Malic Acid | EtOH:H$_2$O (9:1) | White Solid | N/A | Pattern 12A |
| 2162-42-46 | | IPA | Clear Solution | Gel | N/A |
| 2162-42-47 | | Acetone:H$_2$O (9:1) | Clear Solution | Gel | N/A |
| 2162-42-48 | | MeCN | Clear Solution | Gel | N/A |
| 2162-42-49 | L-Latic Acid | EtOH:H$_2$O (9:1) | Clear Solution | Gel | N/A |
| 2162-42-50 | | IPA | Clear Solution | Gel | N/A |
| 2162-42-51 | | Acetone:H$_2$O (9:1) | Clear Solution | Gel | N/A |
| 2162-42-52 | | MeCN | Clear Solution | Gel | N/A |
| 2162-42-53 | L-Aspartic Acid | EtOH:H$_2$O (9:1) | White Solid | N/A | L-Aspartic |
| 2162-42-54 | | IPA | White Solid | N/A | Acid |
| 2162-42-55 | | Acetone:H$_2$O (9:1) | White Solid | N/A | |
| 2162-42-56 | | MeCN | White Solid | N/A | |
| 2162-42-57 | Succinic Acid | EtOH:H$_2$O (9:1) | White Solid | N/A | Pattern 15A |
| 2162-42-58 | | IPA | White Solid | N/A | |
| 2162-42-59 | | Acetone:H$_2$O (9:1) | White Solid | N/A | |
| 2162-42-60 | | MeCN | White Solid | N/A | |
| 2162-42-61 | Sodium | EtOH:H$_2$O (9:1) | White Solid | N/A | β-GPA |
| 2162-42-62 | Hydroxide | IPA | White Solid | N/A | |
| 2162-42-63 | | Acetone:H$_2$O (9:1) | White Solid | N/A | |
| 2162-42-64 | | MeCN | White Solid | N/A | |
| 2162-42-65 | Potassium | EtOH:H$_2$O (9:1) | White Solid | N/A | β-GPA |
| 2162-42-66 | Hydroxide | IPA | White Solid | N/A | |
| 2162-42-67 | | Acetone:H$_2$O (9:1) | White Solid | N/A | |
| 2162-42-68 | | MeCN | White Solid | N/A | |
| 2162-42-69 | Oxalic Acid | EtOH:H$_2$O (9:1) | White Solid | N/A | Pattern 18A |
| 2162-42-70 | | IPA | White Solid | N/A | |
| 2162-42-71 | | Acetone:H$_2$O (9:1) | White Solid | N/A | |
| 2162-42-72 | | MeCN | White Solid | N/A | |
| 2162-45-1 | Magnesium | EtOH:H$_2$O (9:1) | White Solid | N/A | β-GPA |
| 2162-45-2 | Hydroxide | IPA | White Solid | N/A | |

TABLE 11-continued

Results of Salt screening

| Sample ID | Counterion | Solvent | After 24 hours | After Drying | XRPD |
|---|---|---|---|---|---|
| 2162-45-3 | | Acetone:H$_2$O (9:1) | White Solid | | N/A |
| 2162-45-4 | | MeCN | White Solid | | N/A |

EtOH = ethanol;
IPA = isopropanol;
MeCN = acetonitrile

FIGS. 8 through 13 represents the XRPDs of the new crystalline forms isolated from slurry/slow evaporation experiments.

Stage II

The samples that resulted in gels in Stage I of the salt screening experiments were considered for Stage II, where another set of four new solvent systems (methanol, water, ethyl acetate, and trifluoroethanol) were used. The gels were dissolved in the respective solvents (Table 10) at 70° C. and were allowed to stir overnight. If a precipitate was observed the following day the stirring was stopped and XRPD analysis was carried out on the samples. If there was no precipitation, then the samples were dried in the oven at 50° C. Three experiments, hydrobromic acid in methanol and ethyl acetate and L-lactic acid in methanol, resulted in the precipitation β-GPA as confirmed by XRPD analysis. Crystalline forms were prepared with phosphoric acid (from ethyl acetate and trifluoroethanol), methanesulfonic acid (from ethyl acetate), ethanesulfonic acid (from all four solvents), and L-malic acid (from trifluoroethanol).

Example 3. Salt Screening Experiments in 2:1 (β-GPA:Acid) Molar Ratio

Salt screening experiments of β-GPA with maleic, fumaric, and oxalic acids in 2:1 (β-GPA:acid) ratio were set up. Around 0.3 mL of water was used to dissolve β-GPA (120 mg) and the counterion in 2:1 (β-GPA:acid) ratio at 90° C. for oxalic and maleic acid. However, for the experiment with fumaric acid, 0.2 mL of methanol was used to dissolve the counterion at 65° C. All the experiments resulted in the precipitation of white solids within 10 minutes. However, the vials were left for stirring over the weekend. Solids were filtered and rinsed with around 0.5 mL of isopropanol during filtration followed by XRPD analysis. Results are tabulated in Table 12.

Figure 14:
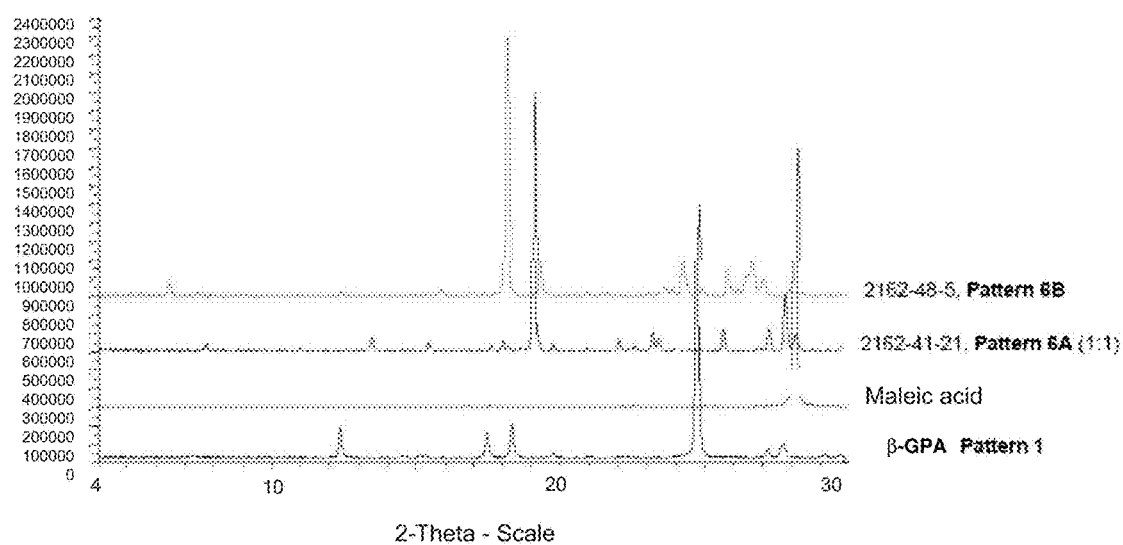
FIG. 14 is an image depicting X-ray powder diffraction (XRPD) pattern obtained for a crystalline form of the 2:1 maleate salt of β-GPA.
Figure 15:
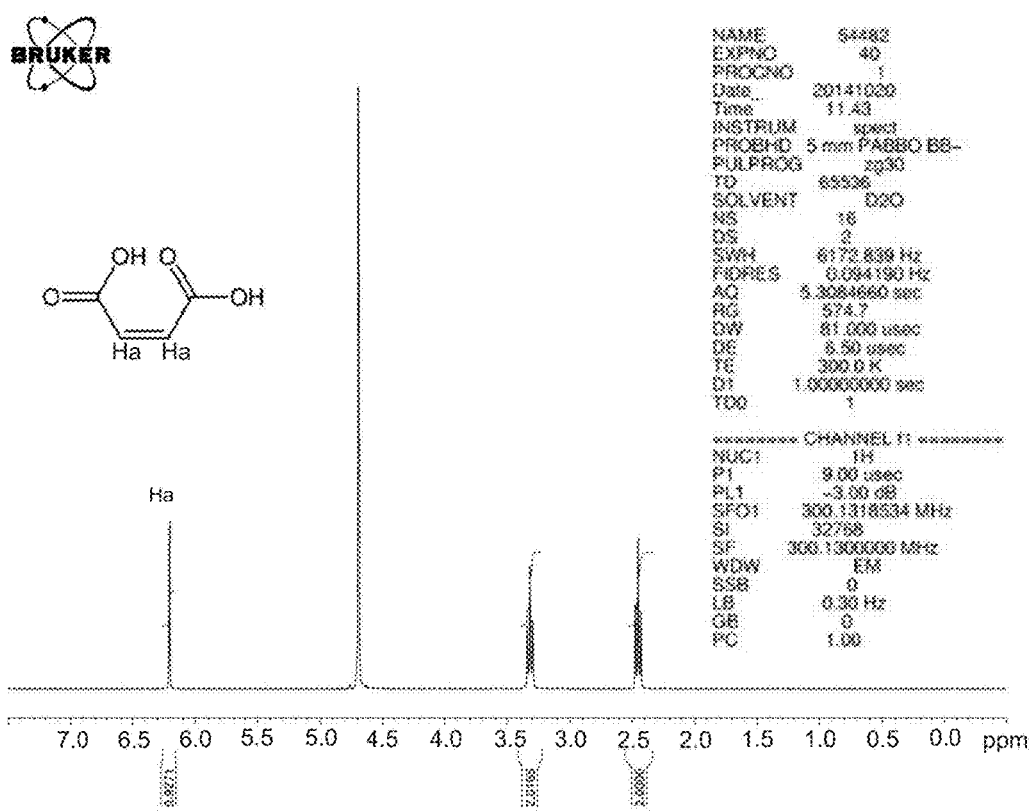
FIG. 15 is an image depicting a $^1$H NMR spectra of a crystalline form of the 2:1 maleate salt of β-GPA.

XRPD analysis revealed a new XRPD pattern for the maleic acid experiment (Pattern 6B, FIG. 14). The 1H-NMR revealed that a 2:1 salt was formed between β-GPA and maleic acid (FIG. 15).

Example 4. Physical and Thermal Characterization of β-GPA

Hydrochloric Acid Salt

Figure 16:
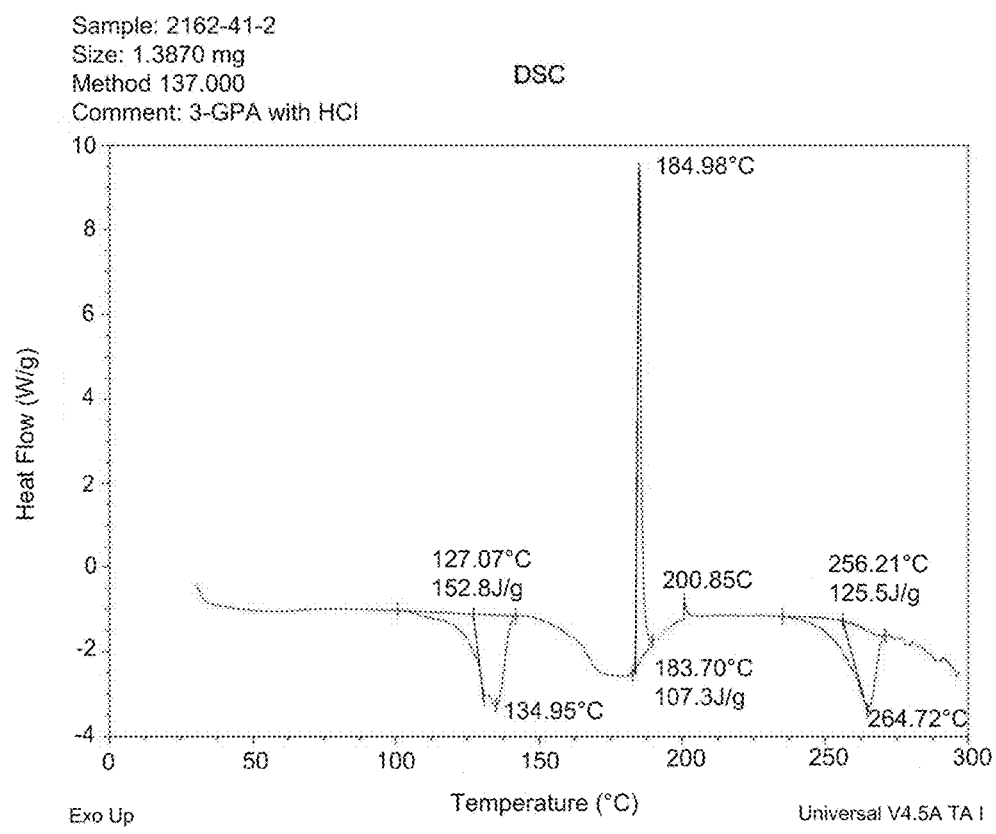
FIG. 16 is an image depicting a DSC thermogram obtained for a crystalline form of the 1:1 hydrochloride salt of β-GPA.
Figure 17:
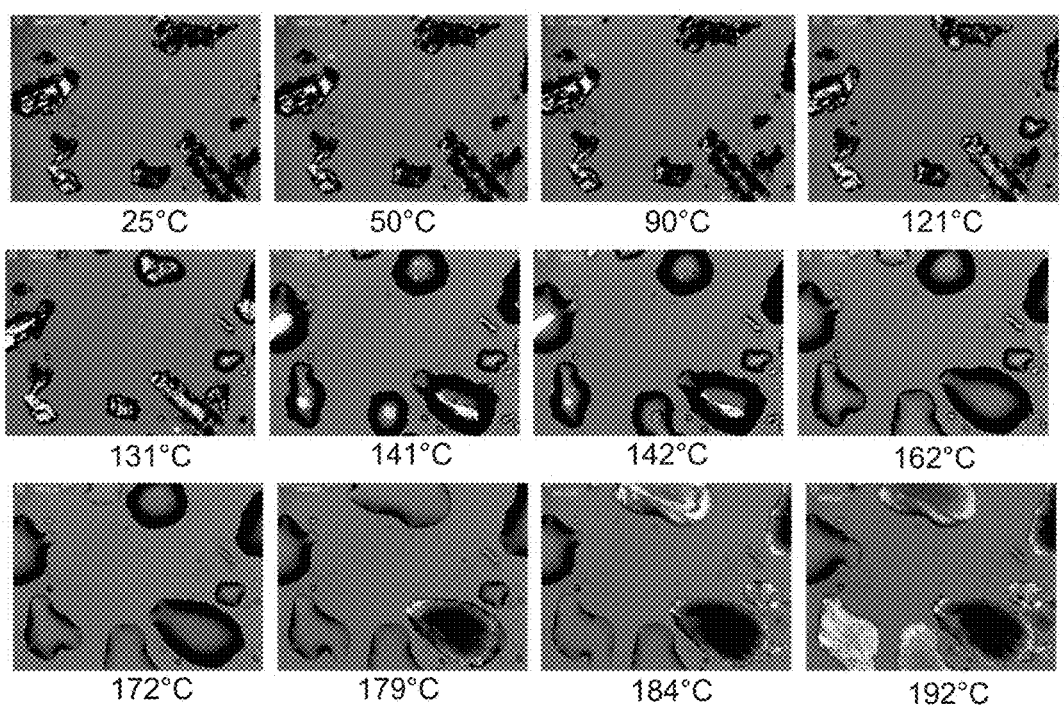
FIG. 17 is an image of a crystalline form of the 1:1 hydrochloride salt of β-GPA by hot stage microscopy.

The DSC of β-GPA-HCl salt (Sample ID: 2162-42-2) revealed the presence of an endothermic event at around 135° C. followed by an exothermic event at around 185° C. and an endotherm at 265° C. (FIG. 16). The exothermic event in the DSC arises from the recrystallization of the sample as confirmed by hot stage microscopy (FIG. 17). The TGA analysis revealed a weight loss of around 11% from 31° C. to 210° C.

Phosphoric Acid Salt

Even though there were some differences in the XRPD patterns of two samples that resulted in crystalline material of β-GPA with phosphoric acid, the DSC and TGA analysis were almost identical. Both samples exhibited a melting point at around 138° C. and a weight loss<1%. The phosphate analysis by Inductively Coupled Plasma/Optical Emission Spectrometry (ICP-OES) for the salt was found to be around 16% (Experimental value: 14%) and therefore it is likely a 1:1 salt.

Maleic Acid Salt (1:1 Salt)

Figure 18:
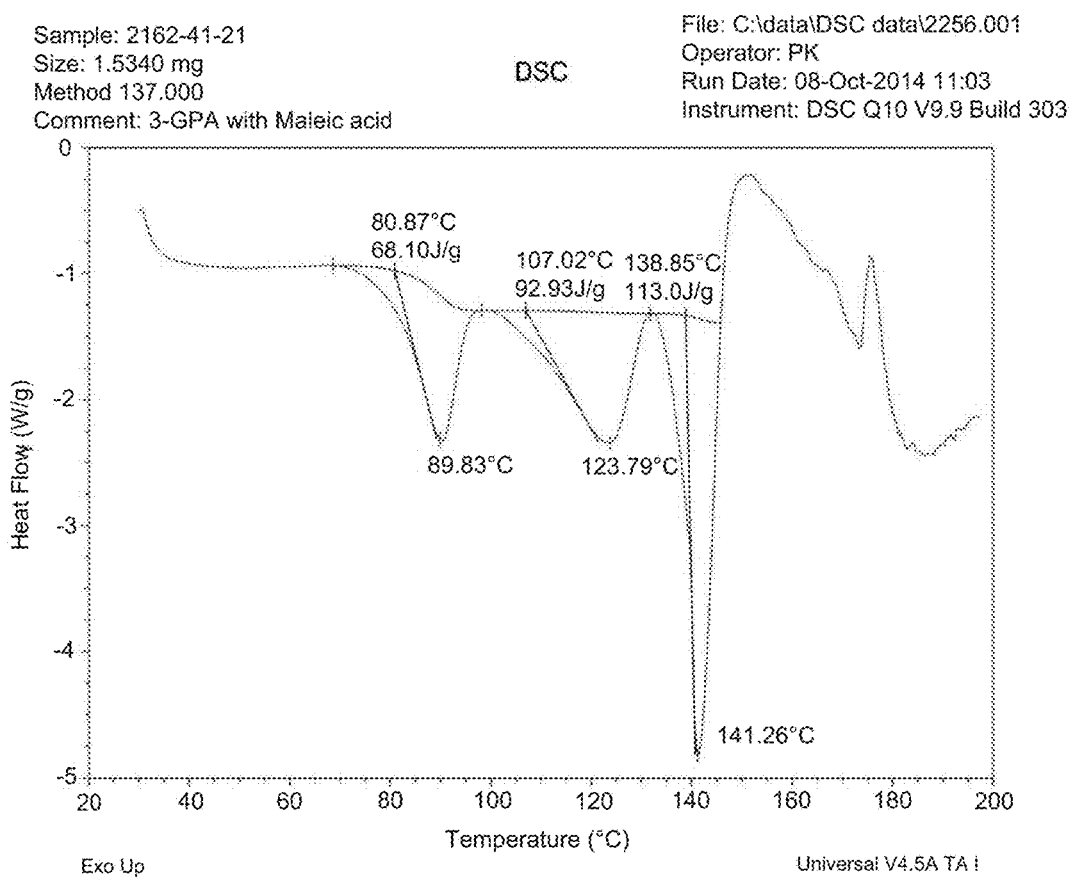
FIG. 18 is an image depicting a DSC thermogram obtained for a crystalline form of the 1:1 maleate salt of β-GPA.

The β-GPA-maleic acid salt (Sample ID: 2162-42-21) exhibited three endotherms at the following temperatures: 90, 124 and 141° C. (FIG. 18). TGA analysis revealed a weight loss of around 1.2% from 31 to 105° C. (1st endotherm) and a weight loss of around 5.4% from 105 to 138° C. (2nd endotherm).

Maleic Acid Salt (2:1 Salt)

The β-GPA-maleic acid salt (Sample ID: 2162-48-6) exhibited two endotherms at 85 and 155° C. respectively. However, the dried sample exhibited only one endotherm at

TABLE 12

Results of Salt Screening Experiments in 2:1 (β-GPA:acid) molar ratio

| Sample ID | Counterion | Ratio of β-GPA to counterion | Solvent(s) used | Result |
|---|---|---|---|---|
| 2162-48-4 | Fumaric acid | 2:1 | 0.3 mL H$_2$O to dissolve β-GPA + 0.2 mL methanol to dissolve fumaric acid | 1:1 salt was formed (Pattern 7A) |
| 2162-48-5 | Oxalic acid | 2:1 | 0.3 mL H$_2$O | Mixture of 1:1 salt and β-GPA |
| 2162-48-6 | Maleic acid | 2:1 | 0.3 mL H$_2$O | 2:1 salt was formed (Pattern 6B) |

155° C. From the DSC analysis it is evident that a hydrate was formed in the prior case whereas an anhydrous form was yielded as a result of drying. TGA analysis revealed a weight loss of <0.1% from 31 to 145° C.

Figure 19:
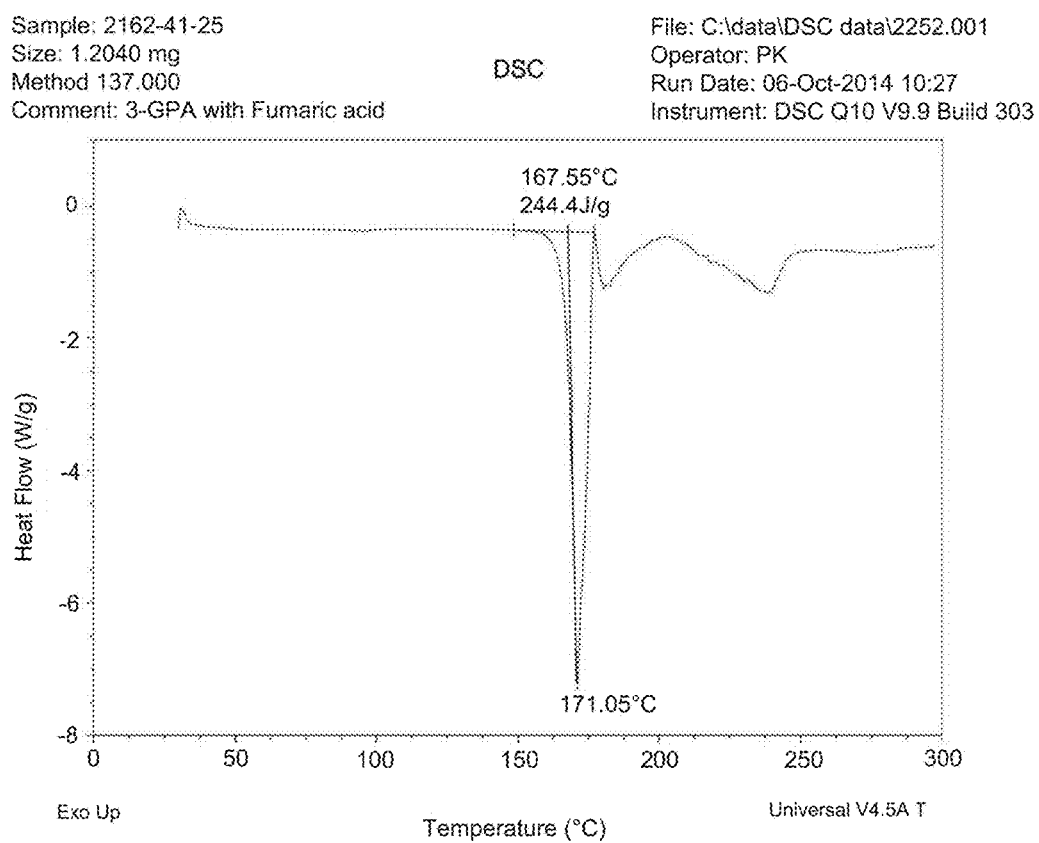
FIG. 19 is an image depicting a DSC thermogram obtained for a crystalline form of the 1:1 fumarate salt of β-GPA.
Figure 20:
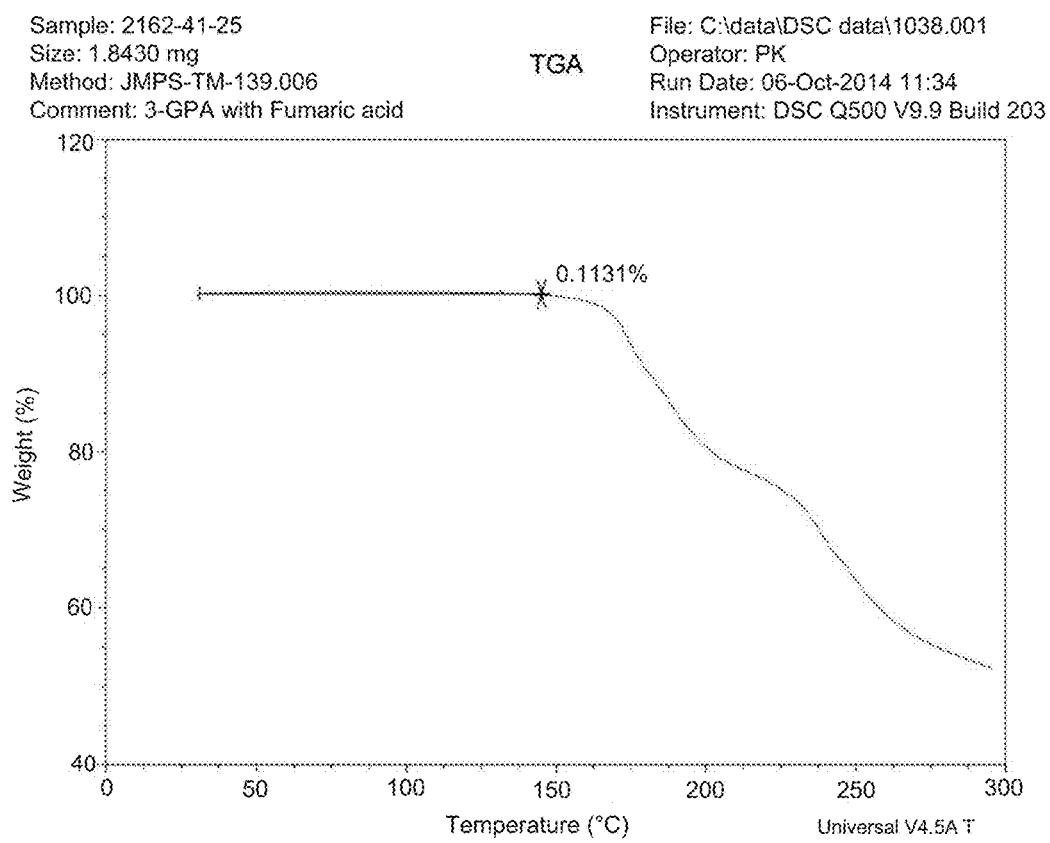
FIG. 20 is an image depicting TGA analysis obtained for a crystalline form of the 1:1 fumarate salt of β-GPA.
Figure 21:
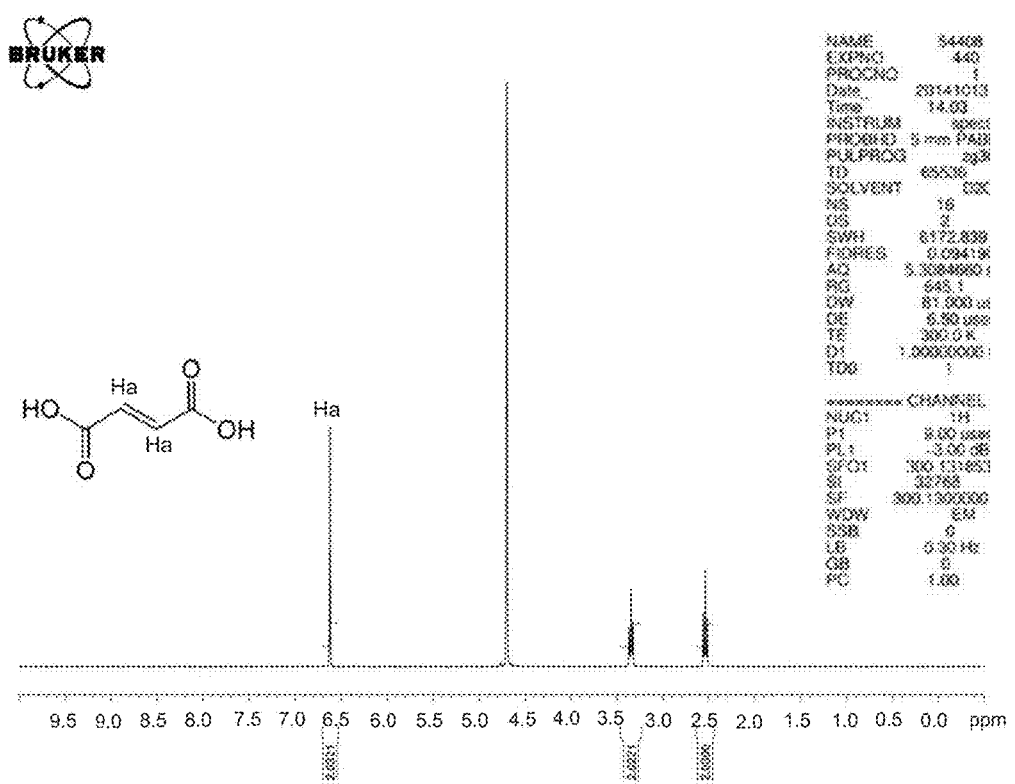
FIG. 21 is an image depicting a $^1$H NMR spectra of a crystalline form of the 1:1 fumarate salt of β-GPA.

Fumaric Acid Salt (1:1 Salt)

β-GPA-fumaric acid salt (Sample ID: 2162-42-25) exhibited an endotherm at 171° C. (FIG. 19) followed by possible decomposition of the salt. TGA analysis revealed a weight loss<1% from 31° C. to 145° C. (FIG. 20). The $^1$H NMR of the 1:1 fumarate salt is shown in FIG. 21.

Ethanesulfonic Acid Salt

The crystalline material that resulted from the experiment between β-GPA and ethanesulfonic acid did not dry out completely even after drying for more than two days in the oven at 50° C. (all the four vials).

When the sample was analyzed by DSC, a broad endothermic event was observed followed by decomposition and the TGA also revealed a weight loss from the starting point (31° C.). The $^1$H-NMR of the sample revealed no traces of ethanesulfonic acid in the sample. Therefore, the crystalline material could have been a product of chemical reaction between β-GPA and ethanesulfonic acid.

L-Malic Acid Salt

β-GPA-L-malic acid salt (Sample ID: 2162-42-45) exhibited an endotherm at 110° C. followed by possible decomposition of the salt. TGA analysis revealed a weight loss<1% from 31° C. to 145° C. The $^1$H-NMR of the salt confirmed it was a 1:1 salt.

Succinic Acid Salt (2:1 Salt)

Figure 22:
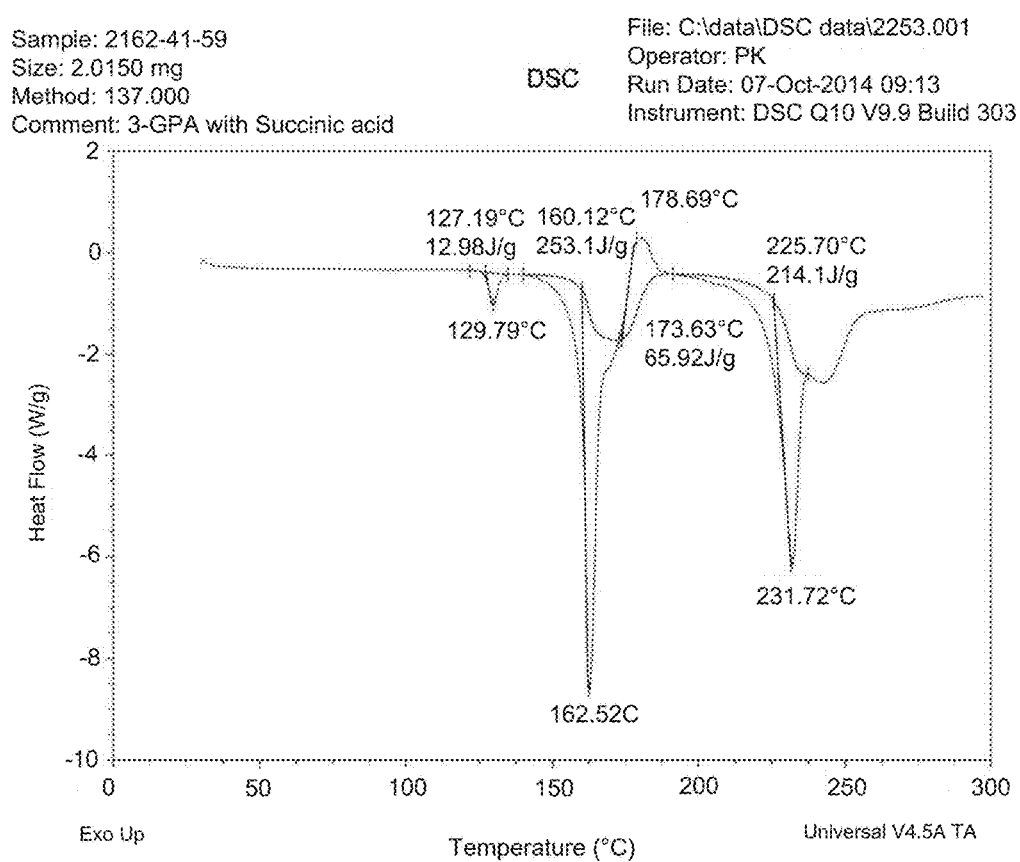
FIG. 22 is an image depicting a DSC thermogram obtained for a crystalline form of the 2:1 succinate salt of β-GPA.
Figure 23:
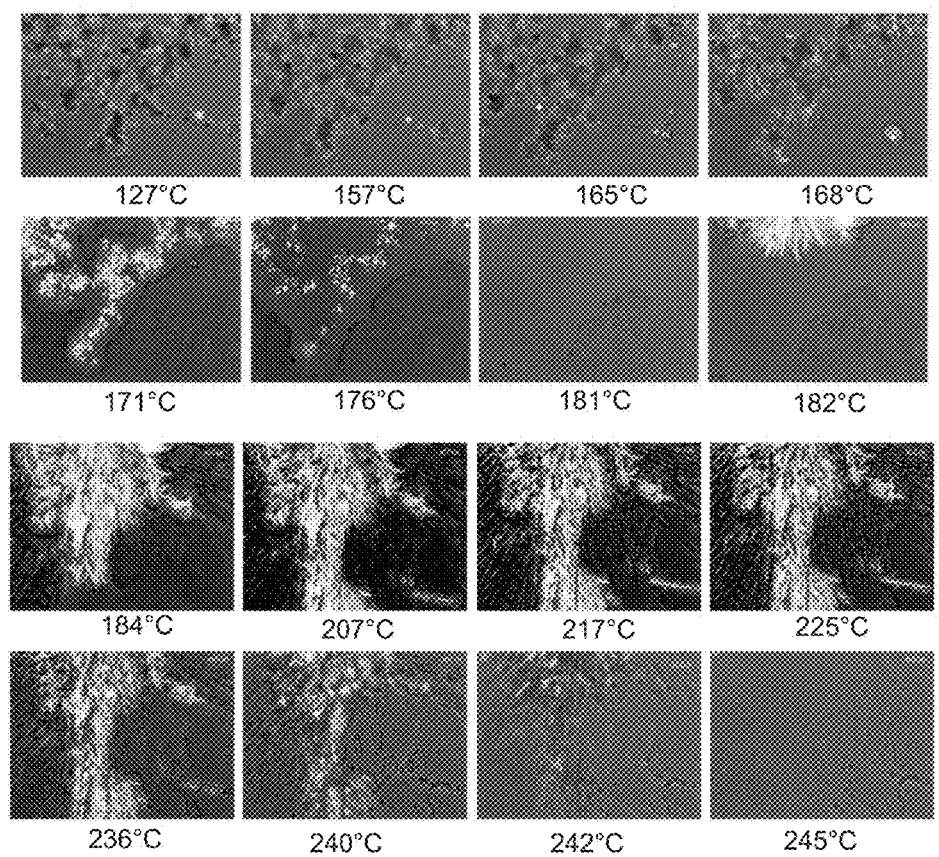
FIG. 23 is an image of a crystalline form of the 2:1 succinate salt of β-GPA by hot stage microscopy.
Figure 24:
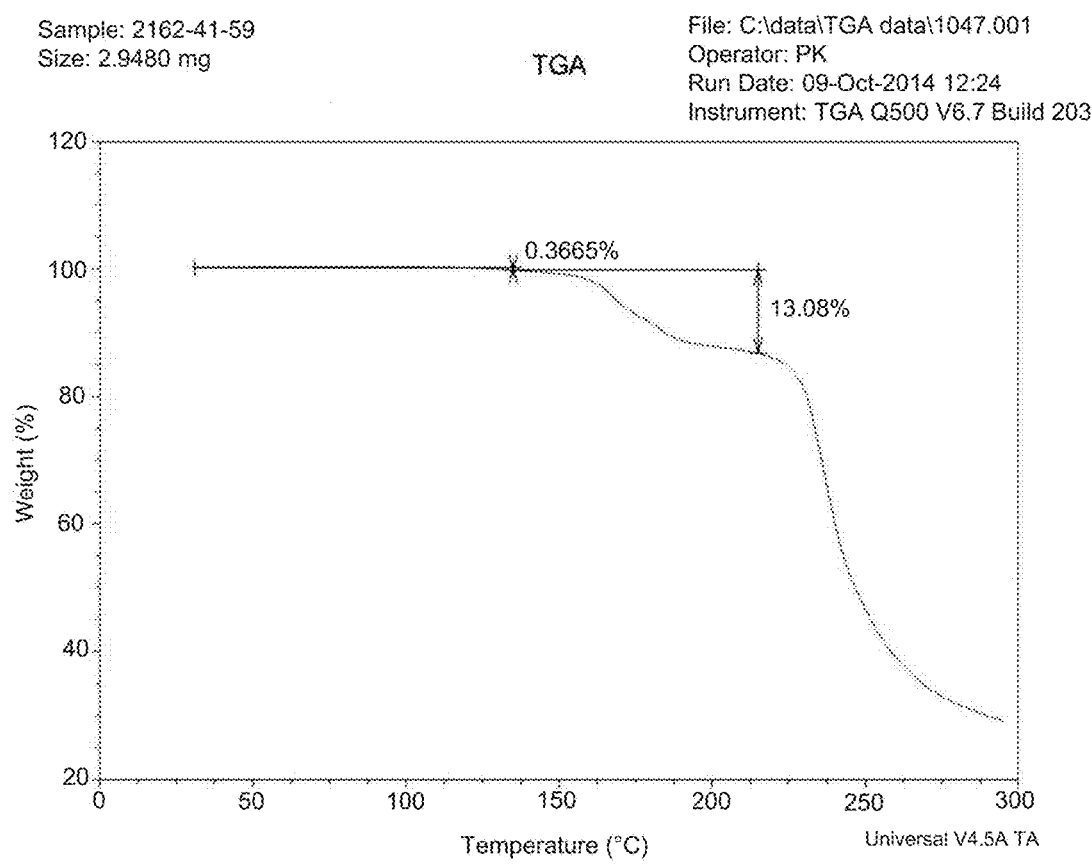
FIG. 24 is an image depicting TGA analysis obtained for a crystalline form of the 2:1 succinate salt of β-GPA.
Figure 25:
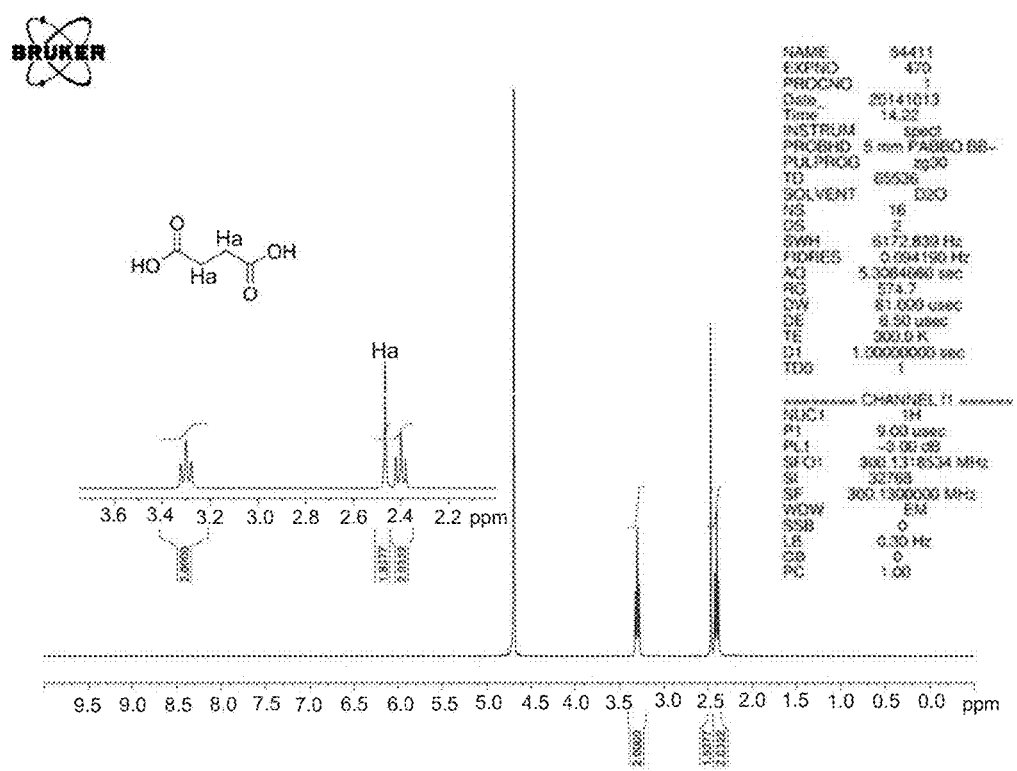
FIG. 25 is an image depicting a ¹H NMR spectra of a crystalline form of the 2:1 succinate salt of β-GPA.

The DSC of β-GPA-succinic acid salt (sample ID: 2162-42-59) revealed the presence of an endothermic event at around 130° C. followed by another endothermic event at around 175° C. An exothermic event was observed at around 179° C. (FIG. 22) followed by an endothermic event at 232° C. To verify the endothermic and exothermic events in the DSC, hot stage microscopy was performed on the sample and illustrated in FIG. 23. The TGA analysis revealed a weight loss of around 0.4% from 31° C. to 135° C. and 13% from 135 to 215° C. (FIG. 24). The $^1$H-NMR revealed that the salt formed between β-GPA and succinic acid was in 2:1 (β-GPA:acid) molar ratio (FIG. 25).

Oxalic Acid Salt (1:1 Salt)

Figure 26:
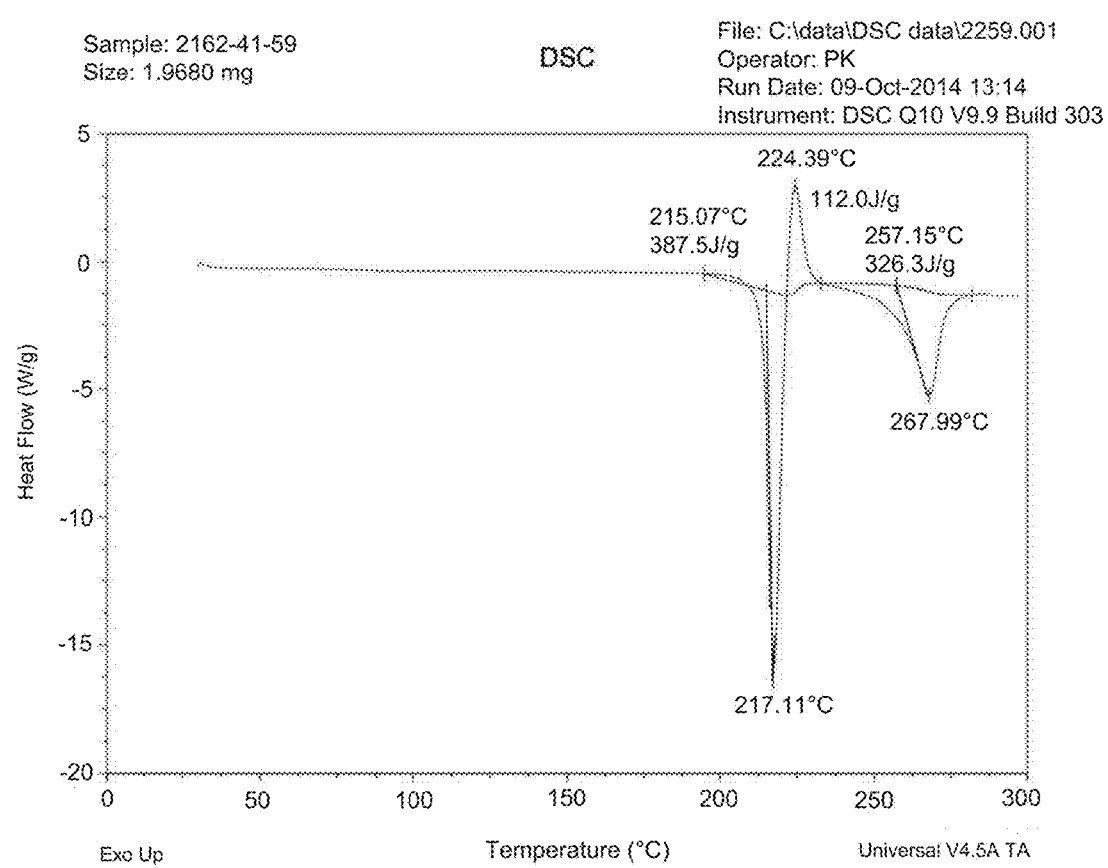
FIG. 26 is an image depicting a DSC thermogram obtained for a crystalline form of the 1:1 oxalate salt of β-GPA.
Figure 27:
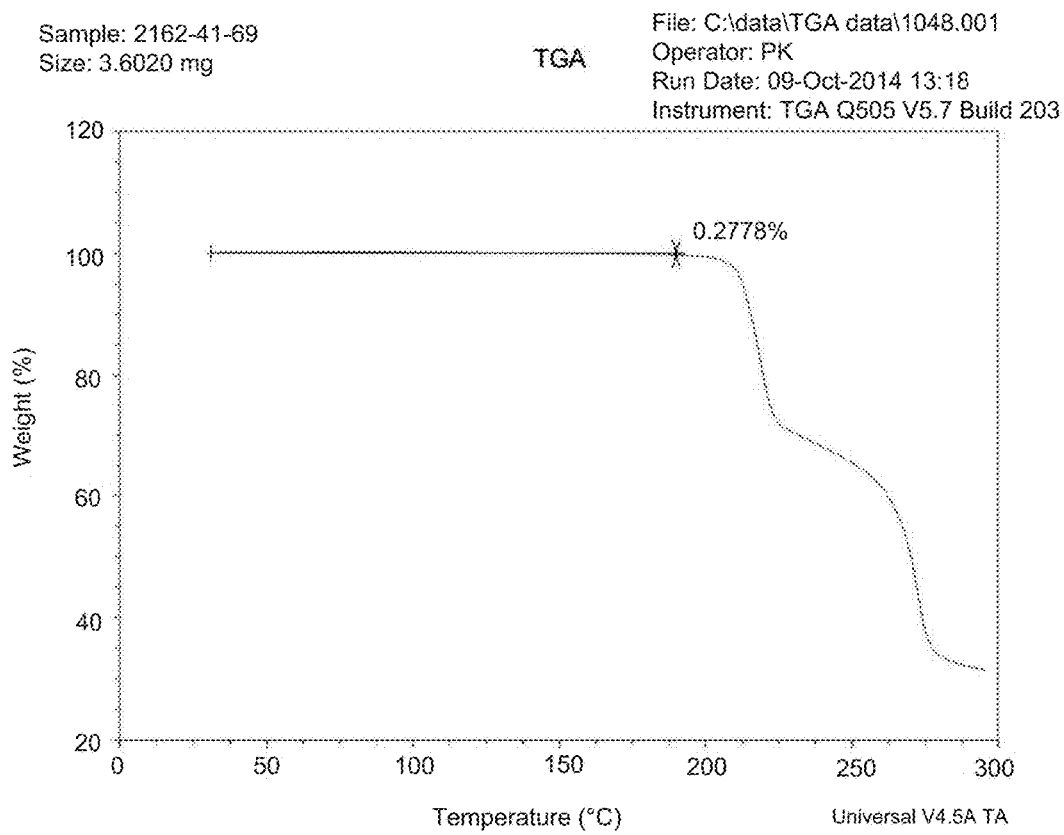
FIG. 27 is an image depicting TGA analysis obtained for a crystalline form of the 1:1 oxalate salt of β-GPA.
Figure 28:
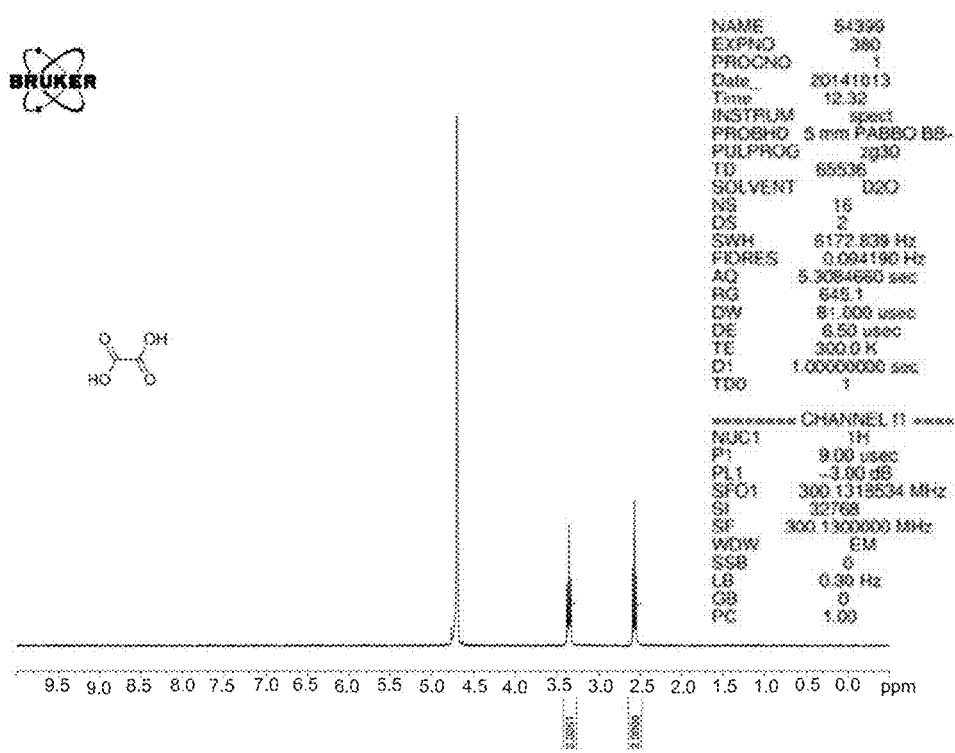
FIG. 28 is an image depicting a ¹H NMR spectra of a crystalline form of the 1:1 oxalate salt of β-GPA.
Figure 29A:
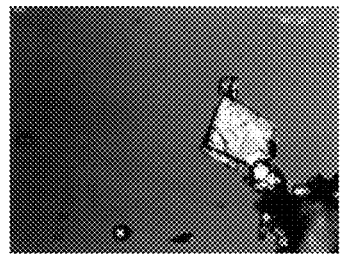
FIG. 29A-FIG. 29J are images of crystalline forms of β-GPA salts.
Figure 29B:
Figure 29C:
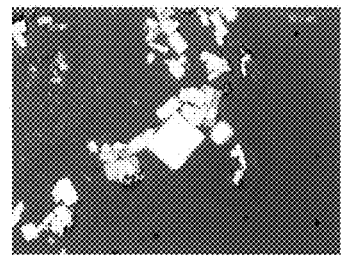
Figure 29D:
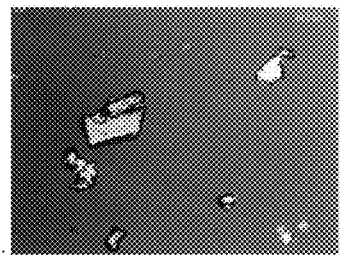
Figure 29E:
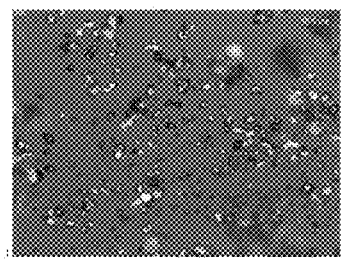
Figure 29F:
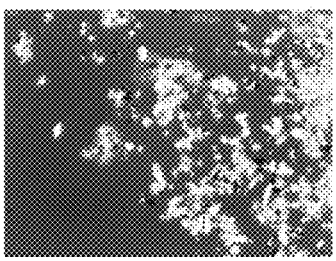
Figure 29G:
Figure 29H:
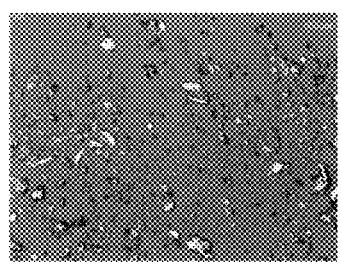
Figure 29I:
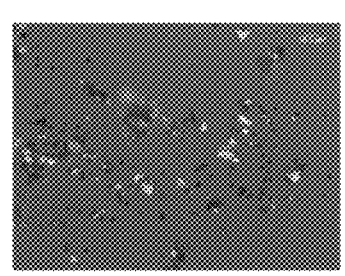
Figure 29J:
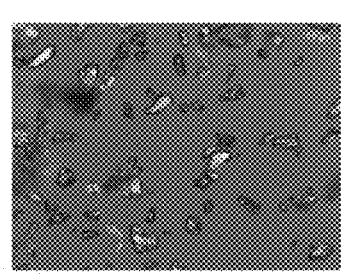

The β-GPA-oxalic acid (Sample ID: 2162-42-69) when analyzed by DSC revealed a presence of an endothermic event at around 217° C. followed by an exothermic peak at around 224° C. and an endotherm at 268° C. as represented in FIG. 26. The TGA analysis revealed a weight loss of <0.3% from 31 to 195° C. (FIG. 27). When the material was observed under hot-stage microscope, at 216 to 226° C. there were very few crystals that appeared to melt however, there was no visible recrystallization event which was observed. From 268° C. melting of the crystals started to occur until 291° C. The $^1$H-NMR of β-GPA oxalate is presented in FIG. 28. From the elemental analysis the stoichiometric ratio of β-GPA to oxalic acid was found to be 1:1 (Intertek).

Example 5. Optical Microscopic Imagery

Figure 30:
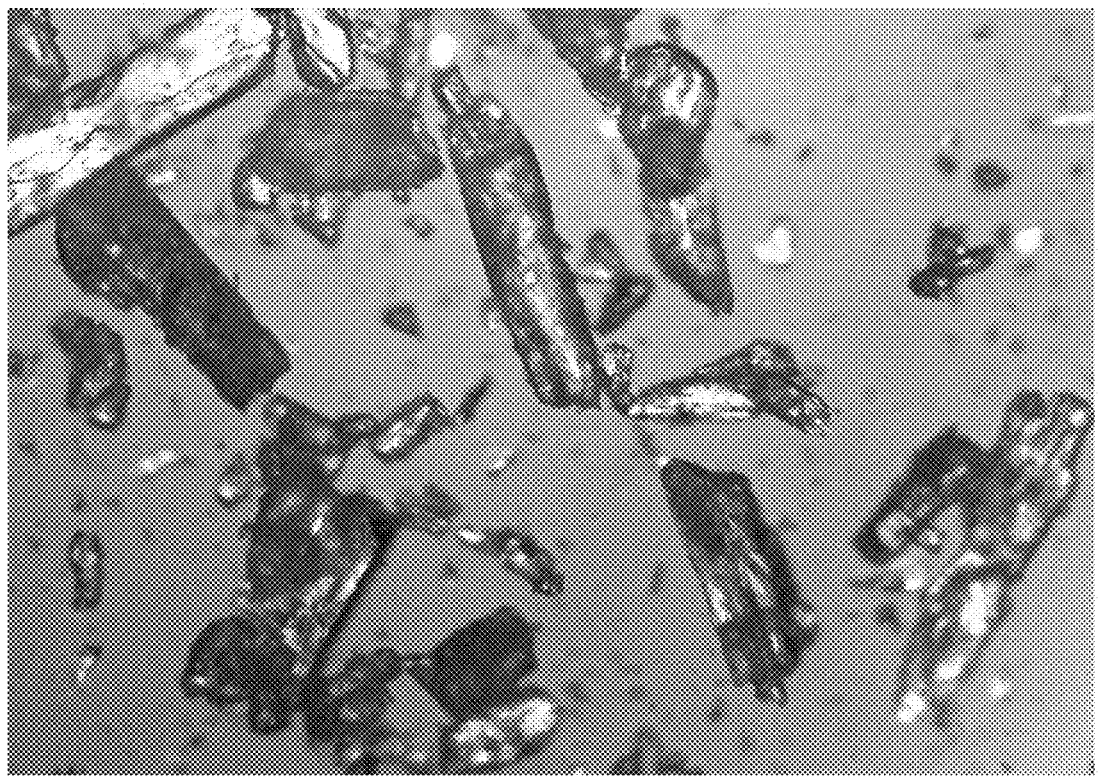
FIG. 30 is an image depicting the rod-like crystal morphology of 1:1 fumarate salt of β-GPA (Pattern 7A).

Salts of β-GPA were also analyzed by optical microscopy. Optical microscopic images of β-GPA salts are presented from FIG. 29A to 29J. As shown in FIG. 30, β-GPA fumarate (1:1) has a rod-like crystal morphology.

Example 6. Stability Testing of 1β-GPA Salts Under Stressed Conditions

The solid form stability of each salt was studied by XRPD under stressed conditions: wet, dry (45° C. under vacuum) and high humidity (RH>95%). The results are tabulated in Table 13.

TABLE 13

Results of Stability Studies

| Salt | Wet_XRPD pattern | Dry_XRPD pattern | Humid_XRPD pattern |
|---|---|---|---|
| β-GPA hydrochloride | Pattern 1A | Pattern 1A | Deliquesce |
| β-GPA phosphate | Pattern 4A | Pattern 4A | Deliquesce |
| β-GPA methanesulfonate | Pattern 19A | Pattern 19A | Deliquesce |
| β-GPA maleate (1:1) Form I | Pattern 6A | Pattern 6A | Pattern 6A |
| β-GPA maleate (1:1) Form II | Pattern 6D | Pattern 6D | Pattern 6D |
| β-GPA maleate (2:1) | Pattern 6B | Pattern 6C | Pattern 6B |
| β-GPA fumarate (1:1) | Pattern 7A | Pattern 7A | Pattern 7A |
| β-GPA malate (1:1) | Pattern 12A | Pattern 12A | Deliquesce |
| β-GPA succinate (2:1) | Pattern 15A | Pattern 15A | Pattern 15A |
| β-GPA oxalate (1:1) | Pattern 18A | Pattern 18A | Pattern 18A |

Example 7. DVS Experiments

Four salts: β-GPA maleate (1:1) Form II, β-GPA fumarate (1:1), β-GPA maleate (2:1), β-GPA succinate (2:1) and β-GPA oxalate (1:1) were analyzed by DVS experiment followed by XRPD analysis of the sample at the end of the experiment.

1:1 β-GPA maleate (Pattern 6D) exhibited an increase in the moisture uptake from 60% RH and at around 95% RH there was around 25% moisture uptake, however, there was no form change after the end of the experiment as confirmed by XRPD.

Figure 31:
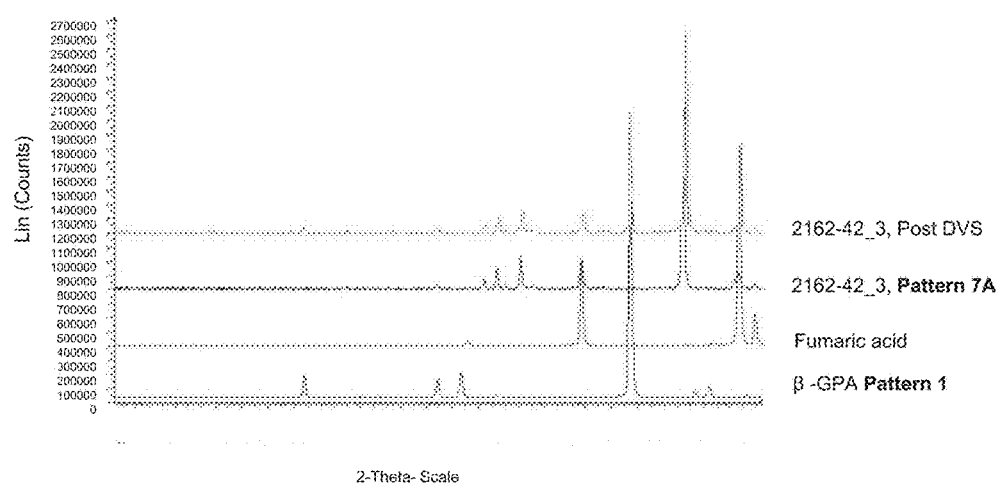
FIG. 31 is an image depicting a comparison of XRPD analysis before and after DVS of 1:1 fumarate salt of β-GPA (Pattern 7A).

1:1 β-GPA fumarate exhibited<1% moisture uptake during the DVS experiment. XRPD analysis on the Post DVS sample revealed the presence of β-GPA peaks along with Pattern 7A (FIG. 31).

Both the 2:1 β-GPA succinate and 1:1 β-GPA oxalate salts revealed<0.5% moisture uptake during the DVS experiment and no form change was observed after the end of the experiment.

Example 8. Solid Form Stability of Salts in Different Solvents

Three salts were studied for solid form stability in water (disproportionation test), methanol, acetonitrile, and acetone:water (9:1) for 48 hours at room temperature.

1:1 β-GPA oxalate and 1:1 β-GPA fumarate salts retained their XRPD pattern after 48 hours slurry in water. 2:1 β-GPA succinate started showing up peaks from β-GPA after 6 hours slurry in water and thus the experiment was stopped after 6 hours.

After slurrying the 1:1 β-GPA fumarate and 1:1 β-GPA oxalate salts in methanol, acetonitrile, and acetone:water (9:1), the salts were found to retain their XRPD pattern.

After slurrying the 2:1 β-GPA succinate in methanol and acetonitrile, the salt was found to retain its XRPD pattern. However, the slurry in acetone:water (9:1) revealed the presence of β-GPA after 48 hours.

Example 9. Solid Form Stability of Salts at 40° C. and 75% Humidity

Solid form stability studies of β-GPA fumarate, succinate, and oxalate were carried out at 40° C. and 75% RH for seven days. Around 30 mg of the salts were placed in 4 mL vials which were placed in a saturated solution of sodium chloride (2 mL) with lids closed at 40° C. The samples were left for a week followed by XRPD analysis of the salts. All three salts retained their original XRPD pattern.

Example 10. Purity of Salts

The purity of β-GPA salts was determined by HPLC using the method below.

The HPLC method is described below:
Column: SeQuant ZIC Hilic PEEK column (250×4.6 mm, 5 μm)
Mobile Phase A: 0.02M Phosphate buffer, pH 3.0
The mobile phase was prepared by dissolving 2.72 g of monobasic potassium phosphate in 1 L of deionized water and the adjusting the desired pH by 85% (w/w) phosphoric acid.
Mobile Phase B: 100% Acetonitrile
Gradient used:

| Time (minutes) | A % | B % |
| --- | --- | --- |
| 0 | 25 | 75 |
| 15.0 | 25 | 75 |
| 23.0 | 80 | 20 |
| 25.0 | 80 | 20 |
| 25.1 | 25 | 75 |
| 30.0 | 25 | 75 |

Flow rate: 1 mL/min
Injection volume: 10 μL
Detector wavelength: 210 nm
Run time: 30 minutes
Column temperature: 40° C.
Diluent: Acetonitrile:water (1:1)

The counterions were also analyzed by HPLC under the same concentrations as they were present in the respective salts.

The purity of β-GPA salts is listed in Table 14.

TABLE 14

Purity of Salts

| β-GPA salt | Purity by HPLC |
| --- | --- |
| β-GPA fumarate (1:1) | 97.7% |
| β-GPA succinate (2:1) | 98.1% |
| β-GPA oxalate (1:1) | 98.4% |

Example 11. Scale-up of Salts

Oxalate Salt

Around 7.2 g (0.055 moles) of β-GPA was added to an EasyMax reaction vessel containing 30 mL water. The reaction mixture was stirred at 90° C. until a clear solution was obtained. To this solution, around 5.4 g (0.06 moles) of oxalic acid was added slowly and the temperature of the reactor was brought down to 20° C. Around 20 mL of isopropanol was added to the reaction mixture was left for overnight stirring. Sample ID: 2162-64-2.

The following day, the slurry was filtered and the solid was washed twice with 10 mL of isopropanol. The cake was placed in a vacuum oven at 45° C. for drying. Yield=11.4 g (94%). The solid was analyzed by XRPD and β-GPA oxalate salt, Pattern 18A, formation was confirmed.

Succinate Salt

Around 72 g (0.55 moles) of β-GPA was added to 400 mL of ethanol:water (9:1) in 500 mL jacketed vessel at 75° C. and a slurry was made. To this, a slurry of succinic acid, prepared by adding 71.2 g (0.6 moles) in 200 mL ethanol:water (9:1) at 65° C., was added. The temperature of the reactor was brought down to 18° C. and the reaction mixture was left for overnight stirring. Sample ID: 2162-62-1.

The following day, the slurry was filtered and the solid was washed twice with 20 mL of isopropanol. The cake was placed in a vacuum oven at 45° C. for drying. Yield=101.3 g (97%). The solid was analyzed by XRPD and the formation of β-GPA succinate (Pattern 15 A) was confirmed.

Fumarate Salt

Around 48 g (0.37 moles) of β-GPA was added to 120 mL of water in 500 mL jacketed vessel at 90° C. and a clear solution was obtained. To this solution, a solution of fumaric acid, prepared by dissolving 46.8 g (0.40 moles) in 220 mL methanol at 65° C., was added. The temperature of the reactor was brought down to 18° C. and the reaction mixture was left for overnight stirring. Sample ID: 2162-64-1.

The following day, the slurry was filtered and the solid was washed twice with 20 mL of isopropanol. The cake was placed in a vacuum oven at 45° C. for drying. Yield=61.5 g (90%). The solid was analyzed by XRPD and the formation of β-GPA fumarate (Pattern 7 A) was confirmed.

Example 12. Determination of Bulk and Tapped Density

The bulk density of β-GPA oxalate (Pattern 18 B), succinate (Pattern 15A), and fumarate (Pattern 7A) were determined by pouring in a known amount of salt (g) into a measuring cylinder. The volume ($V_i$) occupied by the salt was recorded and the bulk density ($\rho_B$) was determined using equation 1.

$$\rho_B = g/V_i \quad (1)$$

The tapped densities of the salts were determined using a Tap density analyzer. A known amount of salt was poured (g) into a measuring cylinder and the initial volume was recorded and tapped using a Tap density analyzer. The final volume ($V_f$) after tapping was recorded and the tapped density ($\rho T$) was calculated by using equation 2.

$$\rho_T = g/V_f \quad (2)$$

Table 15 lists the bulk and tapped density of β-GPA and salts thereof.

TABLE 15

Bulk and Tapped Densities

| Sample | Bulk density (ρB) | Tapped density (ρT) |
| --- | --- | --- |
| β-GPA | 0.389 g/cc | 0.627 g/cc |
| β-GPA oxalate (1:1) | 0.505 g/cc | 0.623 g/cc |
| β-GPA succinate (2:1) | 0.405 g/cc | 0.472 g/cc |
| β-GPA fumarate (1:1) | 0.576 g/cc | 0.613 g/cc |

Example 13. Determination of Carr's Index and Hausner Ratio

Carr's index or Carr's compressibility index (C) is an indication of the compressibility of a powder. It can be calculated using the equation below:

$$\text{Carr's index}(C) = 100(V_i - V_f)/V_i \quad (3)$$

A Carr's index greater than 25 is considered to be an indication of poor flowability while a value below 15 is an indication of good flowability.

The Hausner ratio is a number that is correlated to the flowability of a powder or granular material. It is calculated by using the equation below:

$$\text{Hausner ratio} = V_i/V_f \quad (4)$$

Table 16 lists the Carr's index and Hausner ratio corresponding to the flow character of a powder proposed by R. L. Carl.

TABLE 16

Flow Characteristics Based on Carr's Index and Hausner Ration

| Carr index | Flow character | Hausner ratio |
|---|---|---|
| 1-10 | Excellent | 1.00-1.11 |
| 11-15 | Good | 1.12-1.18 |
| 16-20 | Fair | 1.19-1.25 |
| 21-25 | Passable | 1.26-1.34 |
| 26-31 | Poor | 1.35-1.45 |
| 32-37 | Very poor | 1.46-1.59 |
| >38 | Very very poor | >1.60 |

Table 17 lists the Carr's index and Hausner ratio for β-GPA and salts thereof.

TABLE 17

Carr's Index and Hausner Ratio for β-GPA and Salts Thereof

| Sample | Carr index | Flow character | Hausner ratio |
|---|---|---|---|
| β-GPA | 37.9 | Very very poor | 1.610 |
| β-GPA oxalate (1:1) (Pattern 18 A, original salt) | 18.7 | Fair | 1.23 |
| β-GPA succinate (2:1) (Pattern 15A) | 14.3 | Good | 1.167 |
| β-GPA fumarate (1:1) (Pattern 7A) | 5.9 | Excellent | 1.063 |

Example 14. Flowability Measurement Using Hanson Flodex Unit

Method: A cylindrical vessel is secured to the stand and above that a funnel is also secured such that the bottom of the funnel is close to the vessel. A powder load of ≈50-60 g is then poured through the funnel into the middle of the cylinder. The lever device is pulled to open the hole in the disk quickly and without vibration. If a powder slowly flows through the small-diameter holes, leaving a cavity shaped like an upside-down, truncated cone, the test is considered positive. If a powder flocculates in bulk and falls abruptly, forming a cylindrical cavity, the test is considered negative. If a powder does not fall through the small-diameter holes, the test is considered negative. If the experiment is negative, the powder is tested again with a disk having a larger hole. Tables 18-21 list the flowability test results for β-GPA and salts thereof.

TABLE 18

Flowability Test Results for β-GPA

| Run # | Disc pore Size mm | Did solid pass? |
|---|---|---|
| 1 | 18 | No |
| 2 | 20 | No |
| 3 | 28 | No |
| 4 | 32 | Yes, but the powder fell abruptly forming a cylindrical cavity (flocculation). Thus, the test was considered negative. |
| 5 | 30 | No |
| 6 | 34 | Yes |

TABLE 19

Flowability Test Results for the Oxalate Salt

| Run # | Disc pore Size mm | Did solid pass? |
|---|---|---|
| 1 | 12 | No |
| 2 | 18 | No |
| 3 | 24 | No |
| 4 | 30 | Yes |
| 5 | 28 | Yes |
| 6 | 26 | Yes |

TABLE 20

Flowability Test Results for the Succinate Salt

| Run # | Disc pore Size mm | Did solid pass? |
|---|---|---|
| 1 | 24 | Yes |
| 2 | 22 | Yes |
| 3 | 20 | Yes |
| 4 | 18 | Yes |
| 5 | 10 | Yes |
| 6 | 8 | Yes |
| 7 | 7 | Yes |
| 8 | 5 | No |
| 9 | 6 | No |

TABLE 21

Flowability Test Results for the Fumarate Salt

| Run # | Disc pore Size mm | Did solid pass? |
|---|---|---|
| 1 | 12 | Yes |
| 2 | 6 | Yes |
| 3 | 4 | No |
| 4 | 5 | Yes |

Example 15. DVS and Stability at High Humidity of the 1:1 Fumarate Salt

Sample 2162-64-1 was analyzed by DVS in triplicate and the post DVS samples were characterized by XRPD to identify the form at the end of the experiment. In all the three experiments, the moisture uptake by β-GPA fumarate was found to be less than 0.1%. In all the three experiments, the XRPDs were found to be identical to β-GPA fumarate (Pattern 7A) and no appearance of β-GPA peaks were observed, unlike sample 2162-42-3 post DVS (FIG. 30).

The solid form stability of 2162-64-1 was also studied at RH>95% at room temperature. β-GPA fumarate was found to retain its original XRPD pattern (Pattern 7A) after 48 hours.

Summary of Salt Screening Experiments

Ten salts of β-GPA namely, β-GPA HCl. β-GPA phosphate, β-GPA mesylate, β-GPA maleate (1:1, Pattern 6A), β-GPA maleate (1:1, Pattern 6D), β-GPA maleate (2:1, Pattern 6B), β-GPA fumarate, β-GPA malate, β-GPA succinate and β-GPA oxalate, were isolated from salt screening experiments (Stages I and II).

Of the ten salts, six of the salts, β-GPA HCl, β-GPA phosphate, β-GPA mesylate, β-GPA maleate (1:1, Pattern 6A), β-GPA malate, and β-GPA maleate (2:1, Pattern 6B), were excluded from further studies owing to their deliquescent nature, non-reproducibility, or purity issues.

Three salts of β-GPA were selected after performing the DVS experiments: β-GPA maleate (1:1), fumarate (1:1), succinate (2:1) and oxalate (1:1) and the form stability was determined by XRPD.

β-GPA fumarate, succinate and oxalate retained their XRPD after the DVS experiment. However, β-GPA fumarate revealed the presence of two peaks from the β-GPA indicating dissociation of the salt.

The scaled-up sample of β-GPA fumarate was again analyzed by DVS three times and in these experiments the sample did not exhibit any dissociation of the salt. The previous DVS experiment was disregarded. Additional solid form stability testing of β-GPA fumarate at RH>95% at 20° C. also revealed that the salt was stable.

The purity assessment for the salts was carried out by HPLC and the purity of the salts was as follows: β-GPA fumarate—97.7%, β-GPA succinate—98.1% and β-GPA oxalate—98.4%.

Stability studies of salts were also carried out by slurrying them in water (test for disproportionation), methanol, acetonitrile, and acetone:water (9:1) for 48 hours at room temperature. The following results were obtained:

β-GPA maleate, fumarate and oxalate retained their XRPD patterns after 48 hours slurry in water while, β-GPA succinate showed two peaks from β-GPA after 6 hours slurry in water.

After 48 hours slurry, β-GPA maleate in methanol and acetonitrile was found to retain its XRPD pattern. However, the slurry in acetone:water (9:1) matched with the original pattern of the salt (Pattern 6D) along with some additional peaks in the XRPD analysis.

After 48 hours slurry, β-GPA succinate in methanol and acetonitrile salt was found to retain its original form. However, the slurry in acetone:water (9:1) revealed the presence of β-GPA after 48 hours along with the salt by XRPD analysis.

Solid form stability studies of β-GPA fumarate, succinate, and oxalate were carried out at 40° C. and 75% RH for seven days. All the three salts were found to be stable and retained their original XRPD patterns.

Three salts of β-GPA were scaled up to 60-100 g scale. β-GPA fumarate and succinate were scaled-up successfully; however β-GPA oxalate resulted in an ethanol solvate of the salt (confirmed by $^1$H-NMR). The mole percent of ethanol to β-GPA was found to be 0.22 to 1 (Pattern 18 B).

Nevertheless, by changing the solvent system from ethanol:water (9:1) to water and isopropanol the original β-GPA oxalate salt was produced, but the XPRD pattern confirmed the presence of new additional peaks in minor quantities.

The bulk and tapped densities of β-GPA and its salts: β-GPA oxalate (Patterns 18A and B), fumarate, and succinate were determined using density analyzer unit. Likewise, flowability measurements for the salts were measured using Hanson Flodex unit.

From the experimental data β-GPA and β-GPA oxalate (Pattern 18B) were found to exhibit poor flow character whereas, β-GPA oxalate (Pattern 18A) was fair whilst, β-GPA succinate was good, and β-GPA fumarate exhibited excellent flow characteristics.

Based on the solid form stability, reproducibility, density and flowability properties β-GPA fumarate appears to have the best properties of the salts screened.

Example 16. Polymorph Screening of the 1:1 β-GPA Fumarate Salt

Solid Form Stability of the 1:1 β-GPA Fumarate Salt

The solid form stability of β-GPA fumarate was studied at various temperature/humidity conditions as listed in Table 22 for a week using saturated salt solution chambers. The samples were analyzed by XRPD after a week. The XRPD analysis of the stability samples for β-GPA fumarate under various temperature/RH conditions indicated that β-GPA fumarate retained the original XRPD pattern (Pattern 7A)

TABLE 22

Stability Study Results

| Sample ID | Temperature (° C.) | Relative humidity | Saturated salt solution* | XRPD |
|---|---|---|---|---|
| 2162-75-1 | 20 | 43% | Potassium carbonate | Pattern 7A |
| 2162-75-2 | 20 | 59% | Sodium bromide | Pattern 7A |
| 2162-75-3 | 20 | 73% | Sodium chloride | Pattern 7A |
| 2162-75-4 | 40 | 82% | Potassium chloride | Pattern 7A |
| 2162-75-5 | 60 | 50% | Sodium bromide | Pattern 7A |
| 2162-75-6 | 60 | 80% | Potassium chloride | Pattern 7A |
| 2162-75-7 | 20 | >95% | Water | Pattern 7A |

Solubility of the 1:1 β-GPA Fumarate Salt

Solubility of β-GPA fumarate was measured gravimetrically in fifteen different solvents and solvent mixtures at 15 and 45° C. About 100 mg of the compound was dispensed in ten volumes (1 mL) of the solvent/solvent mixture and slurried for 48 hours. Table 23 represents the solubility of β-GPA fumarate in different solvents. After 48 hours the vials were centrifuged. The supernatant was collected and left for slow evaporation under vacuum at 45° C. and solubility was determined. The solids obtained after centrifugation and evaporation were analyzed by XRPD. The XRPD analysis of the precipitates after 48 hours slurries revealed no form transformations for 1:1 β-GPA fumarate.

TABLE 23

Results of Solubility Study

| Solvent | Temp (° C.) | Sample ID | Solubility (mg/mL) |
|---|---|---|---|
| Water | 15 | 2162-74-1A | 30 |
|  | 45 | 2162-74-1B | >100 |
| IPA:H$_2$O (9:1) | 15 | 2162-74-2A | 1.64 |
|  | 45 | 2162-74-2B | 2.1 |
| MeOH:H$_2$O (9:1) | 15 | 2162-74-3A | 9.2 |
|  | 45 | 2162-74-3B | 11.2 |
| Acetone:H$_2$O (9:1) | 15 | 2162-74-4A | 2.5 |
|  | 45 | 2162-74-4B | 4.1 |
| THF:H$_2$O (9:1) | 15 | 2162-74-5A | 2.08 |
|  | 45 | 2162-74-5B | 4.12 |

TABLE 23-continued

Results of Solubility Study

| Solvent | Temp (° C.) | Sample ID | Solubility (mg/mL) |
|---|---|---|---|
| MeOH | 15 | 2162-74-6A | ~1 |
|  | 45 | 2162-74-6B | 2.73 |
| EtOH | 15 | 2162-74-7A | <1 |
|  | 45 | 2162-74-7B | <1 |
| IPA | 15 | 2162-74-8A | <1 |
|  | 45 | 2162-74-8B | <1 |
| EtOAc | 15 | 2162-74-9A | <1 |
|  | 45 | 2162-74-9B | <1 |
| MeCN | 15 | 2162-74-10A | <1 |
|  | 45 | 2162-74-10B | <1 |
| Acetone | 15 | 2162-74-11A | <1 |
|  | 45 | 2162-74-11B | <1 |
| DCM | 15 | 2162-74-12A | <1 |
|  | 45 | 2162-74-12B | 0.5 |
| Heptane | 15 | 2162-74-13A | <1 |
|  | 45 | 2162-74-13B | <1 |
| TBME | 15 | 2162-74-14A | 3.0 |
|  | 45 | 2162-74-14B | 28.9 |
| $H_2O$:MeOH:IPA (3:5.5:5) | 15 | 2162-74-15A | <1 |
|  | 45 | 2162-74-15B | <1 |

Figure 32:
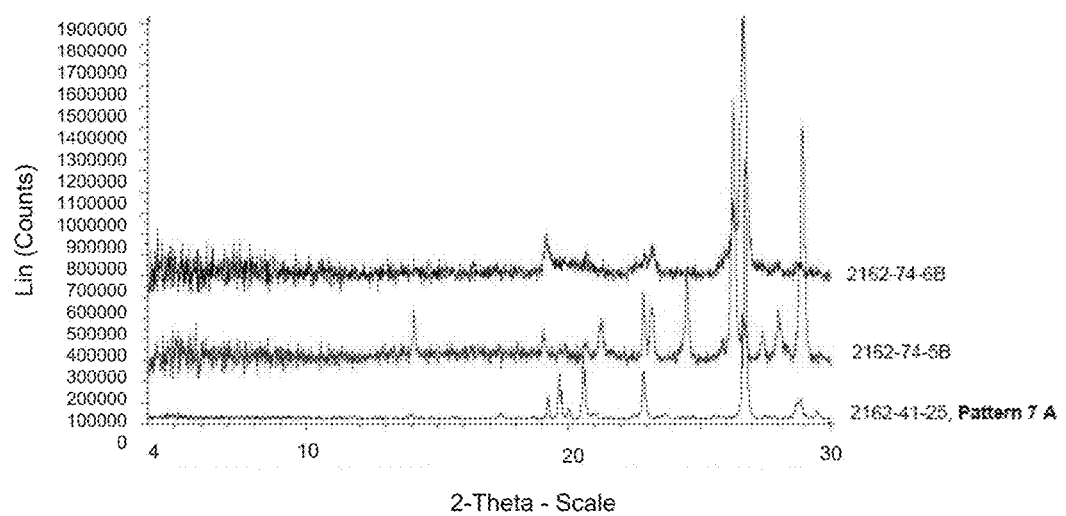
FIG. 32 is an image depicting X-ray powder diffraction (XRPD) pattern obtained for a crystalline form of the 1:1 fumarate salt of β-GPA after slow evaporation of solvent.
Figure 33:
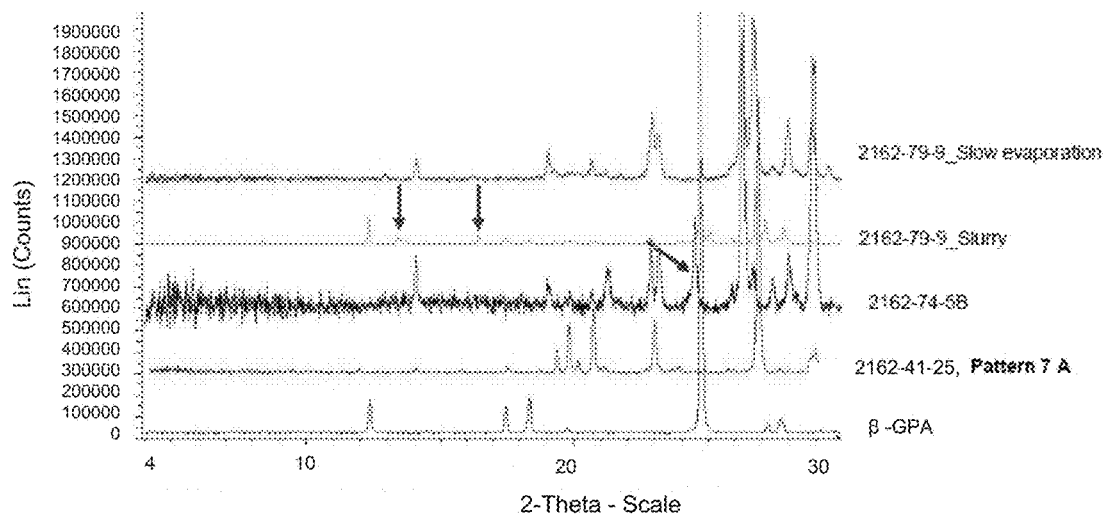
FIG. 33 is an image depicting an X-ray powder diffraction (XRPD) pattern obtained for a crystalline form of the 1:1 fumarate salt of β-GPA after slurry experiment in tetrahydrofuran:water (1:1) for 48 hours.

IPA = isopropanol;
EtOH = ethanol;
EtOAc = ethyl acetate;
DCM = dichloromethane;
TBME = t-butylmethyl ether;
MeOH = methanol;
MeCN = Acetonitrile For ten of fourty-five samples the XRPDs after the slow evaporation of the filtrates from the slurry experiments resulted in Pattern 7A. Seventeen samples did not have enough solids for XRPD analysis. Sample 2162-74-5B resulted in a new crystalline form after slow evaporation of the filtrate and sample 2162-74-6B resulted in mixed XRPDs of Patterns 7A and 7B (FIG. 32).

β-GPA fumarate was slurried in tetrahydrofuran:water (1:1) for 48 hours. The filtrate was set up for evaporation at 45° C. under vacuum, and after overnight evaporation an off-white solid was obtained. Both the solids from the slurry and the solids obtained after slow evaporation were analyzed by XRPD (FIG. 33).

Pattern 7B, obtained by slow evaporation (45° C.) of the filtrate of β-GPA fumarate from the slurry experiment in tetrahydrofuran:water (1:1), was analyzed by DSC and $^1$H-NMR. The DSC revealed the presence of an endotherm at 161° C. and also traces of Pattern 7A (the original β-GPA fumarate salt).

Anti-solvent Addition Experiments

Anti-solvent addition experiments for 1:1 β-GPA fumarate were performed by using different anti-solvents. A given amount of 1:1 β-GPA fumarate was dissolved in the solvent at 50° C. Around 1 mL of ice cold anti-solvent was added to salt solution and continued stirring in ice bath for 2 hours followed by overnight stirring at 20° C. None of the experiments resulted in a new form of β-GPA fumarate.

Neat and Solvent Drop Grinding Experiments

Neat and solvent drop grinding experiments were also performed as a part of polymorph screening. Around 30 mg of the sample was ground in the presence of 20 µL of solvent (tetrahydrofuran, isopropanol, acetone, water, or t-butylmethylether) for 5 minutes using mortar and pestle. After grinding, the samples were analyzed by XRPD. All the experiments resulted in XRPDs that were identical to Pattern 7A.

Figure 34:
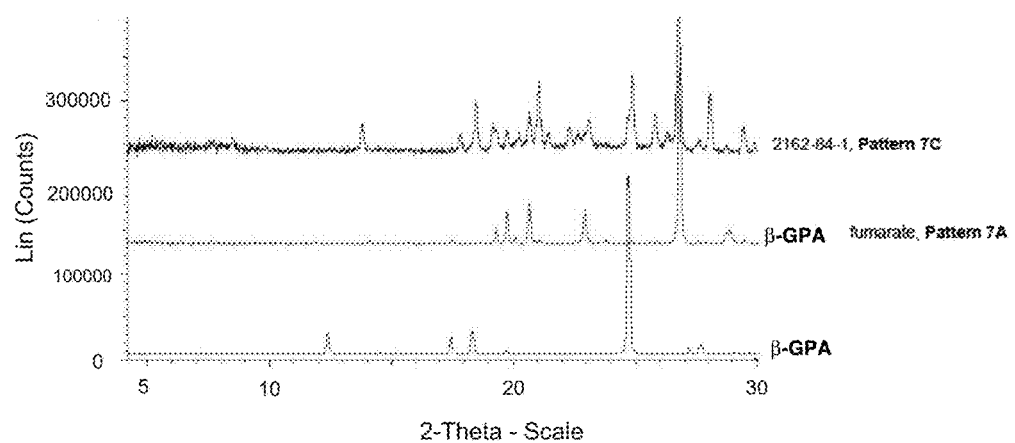
FIG. 34 is an image depicting X-ray powder diffraction (XRPD) pattern obtained for a crystalline form of the 2:1 fumarate salt of β-GPA.
Figure 35:
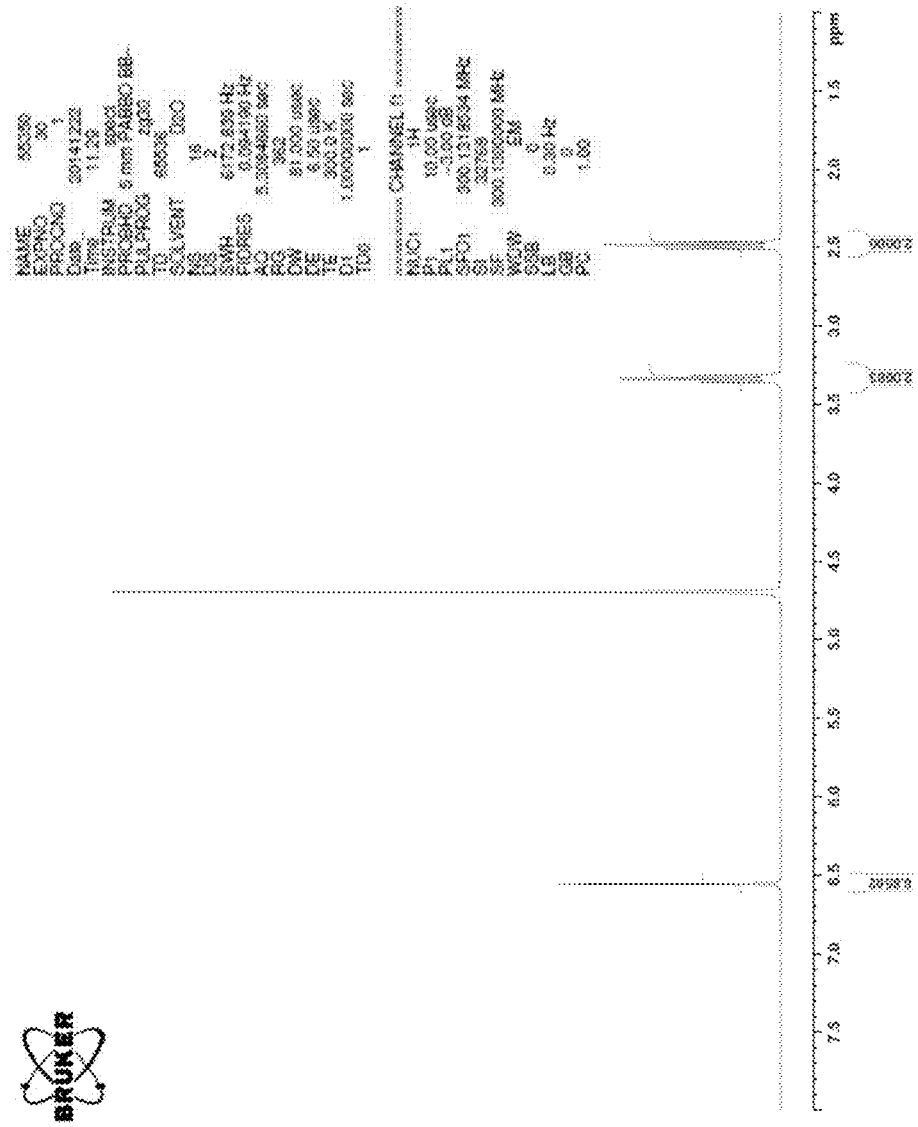
FIG. 35 is an image depicting a ¹H NMR spectra of a crystalline form of the 2:1 fumarate salt of β-GPA.

Attempts to Generate Amorphous Form of β-GPA Fumarate 1 g of 1:1 β-GPA fumarate was dissolved in 10 mL of water at 50° C. in a round bottom flask. The round bottom flask was placed in the dry ice/acetone cooling bath (−78° C.) until the sample solidified followed by lyophilization for 48 hours. A white solid was obtained which was analyzed by XRPD, DSC and $^1$H-NMR. Sample ID: 2162-84-1. The XRPD analysis revealed a new XRPD pattern for 2162-84-1 (Pattern 7C) as shown in FIG. 34. The 1H-NMR of 2162-84-1 revealed that the solid obtained after lyophilization resulted in the formation of 2:1 β-GPA fumarate (FIG. 35). However, the microscopic image of the sample revealed the presence of some amorphous material. It could be possible that excess of fumaric acid after the formation of 2:1 β-GPA fumarate salt might have transformed to amorphous as seen in the microscopic image of the lyophilized sample To confirm the above hypothesis the following experiments (Table 24) were performed on the lyophilized sample (Pattern 7C):

TABLE 24

Results of Experiments Performed on 2:1 Fumarate Salt

| Sample ID | Experiment | Result |
|---|---|---|
| 2162-86-2 | 10 mg of Pattern 7C (lyophilized sample) and Pattern 7A were mixed in a vial and left undisturbed at room temperature (48 hours). The mixture was later analyzed by XRPD. | Pattern 7C to Pattern 7A |
| 2162-86-3 | Vial containing 20 mg of Pattern 7C was heated at 50° C. 5-10 minutes and later analyzed by XRPD. | Pattern 7C to Pattern 7A |
| 2162-86-4 | Vial containing 20 mg of Pattern 7C was placed in a humidity chamber with RH >95% for 48 hours. Sample was later analyzed by XRPD. | Pattern 7C to Pattern 7A |
| 2162-87-1 | 50 mg of Pattern 7C was slurried in 0.2 mL of water. | Pattern 7C to Pattern 7A (within 10 minutes) |

Figure 36:
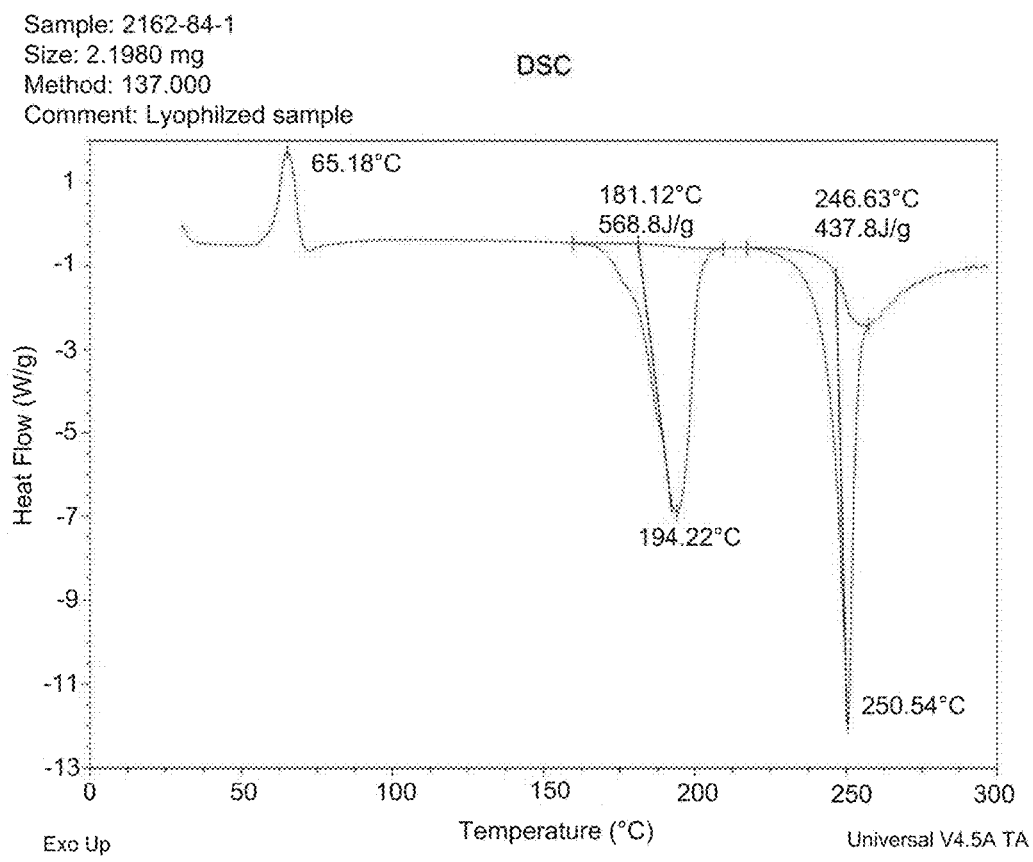
FIG. 36 is an image depicting a DSC thermogram obtained for a crystalline form of the 2:1 fumarate salt of β-GPA.

The DSC of the lyophilized sample revealed the presence of an exothermic event (possible recrystallization or solid phase transformation) followed by two endothermic events (FIG. 36). The first endothermic event could be the 1:1 β-GPA fumarate salt followed by the melting of possible side product which might have formed after the melting of 1:1 β-GPA fumarate salt.

1 g of 1:1 β-GPA fumarate was dissolved in 10 mL of water at 50° C. and was placed under vacuum at 100° C. for fast evaporation. Sample ID: 2162-84-2. The solid obtained was analyzed by XRPD and sample was found to retain the original β-GPA fumarate powder pattern (Pattern 7A).

Temperature Cycling Experiments

The following (Table 25) experiments were performed to isolate possible polymorphic forms of 1:1 β-GPA fumarate.

TABLE 25

Temperature Cycling Results

| Sample ID | Experiment | Result |
|---|---|---|
| 2162-84-3 | Vial containing 50 mg of β-GPA fumarate was placed in vacuum oven at 130° C. for 2 hours and brought to room temperature (RT) and placed back in the oven at 130° C. for 48 hours and again to RT. | Pattern 7A |
| 2162-84-4 | Vial containing 50 mg of β-GPA fumarate was placed on the hot plate at 50° C. for 2 hours and brought to room temperature and placed back in the oven at 50° C. for 48 hours and again to RT. | Pattern 7A |
| 2162-84-5 | Vial containing 50 mg of β-GPA fumarate was placed in the dry ice-acetone mixture for 30 minutes and was brought to room temperature and again placed back in the dry ice-acetone mixture for additional 30 min and again to RT. | Pattern 7A |
| 2162-84-6 | 50 mg of β-GPA fumarate was heated in a vial to 150° C. and brought to room temperature. This cycle was repeated three times and the sample was analyzed later by XRPD. | Pattern 7A |
| 2162-84-7 | 50 mg of β-GPA fumarate was heated in an aluminum cup to 165° C. and immediately placed in dry ice/acetone cooling bath for 15 min. Later, the sample was analyzed later by XRPD. | The started turned yellow to brown in color upon heating. Pattern 7D |

Heating of β-GPA fumarate (2162-84-7) at 160-165° C. resulted in a yellow to brownish solid (possible side reaction followed by decomposition) which was further analyzed by 1H-NMR and XRPD.

Several cooling experiments were conducted all of which resulted in no form change, or resulted in the isolation of fumaric acid-β form or a mixture of fumaric acid-α and β forms concomitantly.

Lyophilization Experiments to Form the 2:1 Salt

Around 264 mg of β-GPA and 118 mg fumaric acid were dissolved in 10 mL of water at 65° C. The solution was solidified using dry ice-acetone mixture followed by freeze drying for 48 hours. This resulted in the isolation of the 2:1 salt.

Diffusion Experiments

Diffusion experiments for 1:1 β-GPA fumarate were set up dissolving around 1 g of the salt in 10 mL of water. For every diffusion experiment, 1 mL of the above solution was dispensed in a small 4 mL vial and was placed in a 20 mL scintillation vial containing the different solvents. None of the experiments resulted in a new form of β-GPA fumarate.

Reverse Anti-Solvent Addition Experiments

Reverse anti-solvent addition experiments for 1:1 β-GPA fumarate were performed by using different anti-solvents. A given amount of 1:1 β-GPA fumarate was dissolved in 1 mL of solvent at 40° C. This solution was added to a known amount of an anti-solvent and stirred at room temperature until solids precipitated out. None of the experiments resulted in a new form of β-GPA fumarate.

Summary of Polymorph Screening Experiments

Based on the available data obtained from the screening experiments, Pattern 7A (the original 1:1 β-GPA fumarate form) appears to be the most stable form.

Example 17. Raman Spectroscopy of 1:1 β-GPA Fumarate Salt

Figure 37:
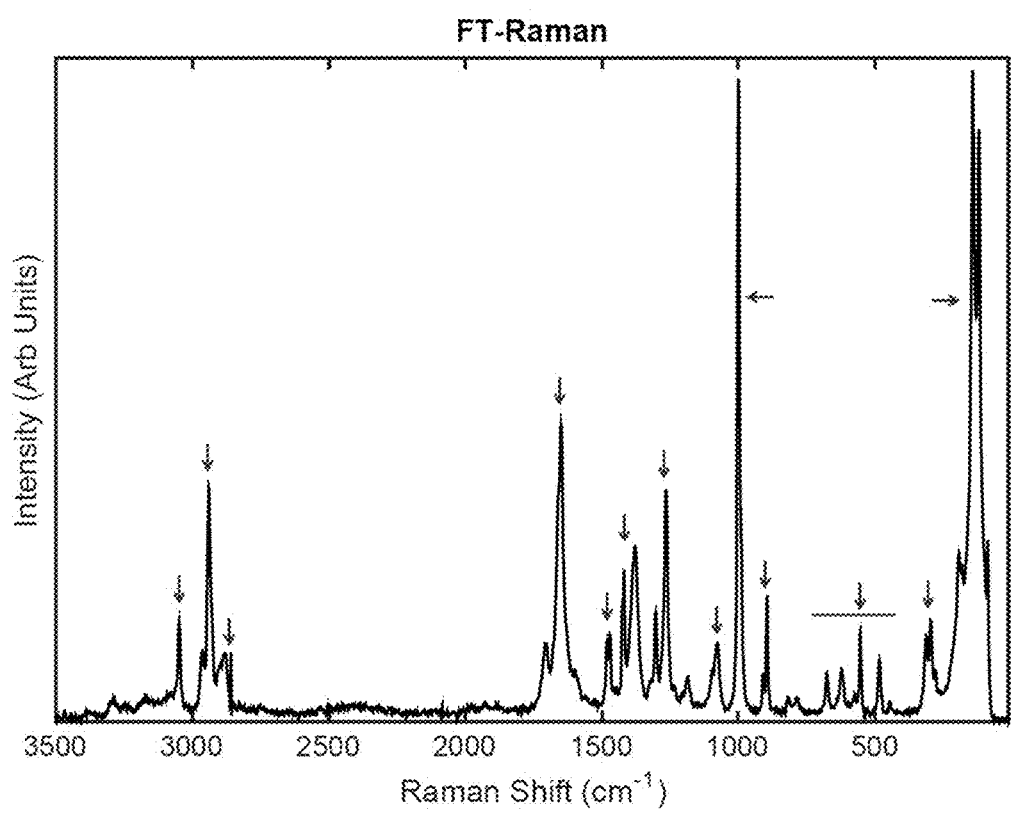
FIG. 37 is an image depicting the Raman spectra of a crystalline form of the 1:1 fumarate salt of β-GPA.

Raman spectroscopy of the 1:1 β-GPA fumarate salt (Pattern 7A) was carried out on a Bruker IFS 66V/S FT-IR/FT-Raman spectrometer equipped with a 1064 nm laser (FIG. 37). The peak list of the Raman spectra is listed in Table 26.

TABLE 26

Raman Spectra Peak List 1:1 fumarate β-GPA fumarate salt

| Raman Shift (cm−1) | Functional group |
|---|---|
| 3300.48 | COOH/NH |
| 3188.58 | |
| 3049.73 | C=C—H |
| 2941.74 | CH2 |
| 2886.78 | |
| 1713.28 | C=O, υ(C=C), υ(C=N) |
| 1653.49 | |
| 1483.79 | N=N—R |
| 1421.11 | N=N |
| 1382.54 | |
| 1305.4 | Alkene In-plane bending |
| 1268.76 | |
| 1190.66 | Alkene out of plane bending |
| 1084.59 | C—C (acid) |
| 997.81 | |
| 896.56 | υ(O—O) |
| 681.53 | |
| 625.6 | Aliphatic chain vibrations |
| 555.21 | |
| 486.79 | δ(CC) aliphatic chains |

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features herein before set forth.

What is claimed is:

1. A method of treating cancer expressing SLC6a8 and CKB in a subject in need thereof, said method comprising administering an effective amount of a pharmaceutically acceptable salt of β-guanidinopropionic acid to said subject, wherein the pharmaceutically acceptable salt of β-guanidinopropionic acid is a 2:1 succinate salt.

2. The method of claim 1, wherein said cancer is metastatic cancer.

3. The method of claim 2, wherein said effective amount comprises an amount effective to suppress metastatic colonization of said cancer.

4. The method of claim 3, wherein said cancer is gastrointestinal cancer.

5. The method of claim 1, wherein said subject is identified to have, or to be at risk of having, metastatic cancer on the basis of the expression level of CKB and/or SLC6a8 being above a predetermined reference value.

6. A method for treating metastatic cancer expressing SLC6a8 and CKB in a subject in need thereof, comprising injecting into the subject an aqueous composition comprising a pharmaceutically acceptable salt of β-guanidinopropionic acid and a pharmaceutically acceptable excipient in an amount effective to suppress metastatic colonization of said cancer, wherein the pharmaceutically acceptable salt of β-guanidinopropionic acid is a 2:1 succinate salt.

7. The method of claim 6, wherein said metastatic cancer is gastrointestinal cancer.

8. A method of treating cancer in a subject in need thereof comprising:
    (a) providing a subject identified to have, or to be at risk of having, metastatic cancer on the basis of the expression of CKB and/or SLC6a8 in the cancer; and
    (b) administering to the subject an effective amount of a pharmaceutically acceptable salt of β-guanidinopropionic acid, wherein the pharmaceutically acceptable salt of β-guanidinopropionic acid is a 2:1 succinate salt.

9. The method of claim 8, wherein said metastatic cancer is gastrointestinal cancer.

10. The method of claim 1, further comprising administering an additional therapy.

11. The method of claim 10, wherein the additional therapy comprises irinotecan, leucovorin, oxaliplatin, and/or 5-FU.

12. The method of claim 6, further comprising administering an additional therapy.

13. The method of claim 12, wherein the additional therapy comprises irinotecan, leucovorin, oxaliplatin, and/or 5-FU.

14. The method of claim 8, further comprising administering an additional therapy.

15. The method of claim 14, wherein the additional therapy comprises irinotecan, leucovorin, oxaliplatin, and/or 5-FU.

* * * * *